(12) United States Patent
Rössl

(10) Patent No.: US 9,861,330 B2
(45) Date of Patent: Jan. 9, 2018

(54) DIFFERENTIAL PHASE-CONTRAST IMAGING

(75) Inventor: Ewald Rössl, Ellerau (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 676 days.

(21) Appl. No.: 13/878,841

(22) PCT Filed: Oct. 17, 2011

(86) PCT No.: PCT/IB2011/054580
§ 371 (c)(1),
(2), (4) Date: Apr. 11, 2013

(87) PCT Pub. No.: WO2012/052900
PCT Pub. Date: Apr. 26, 2012

(65) Prior Publication Data
US 2013/0202081 A1     Aug. 8, 2013

(30) Foreign Application Priority Data
Oct. 19, 2010   (EP) .................................. 10187975

(51) Int. Cl.
*A61B 6/00*    (2006.01)
*G21K 1/06*    (2006.01)
(Continued)

(52) U.S. Cl.
CPC .............. *A61B 6/484* (2013.01); *A61B 6/032* (2013.01); *A61B 6/4035* (2013.01);
(Continued)

(58) Field of Classification Search
CPC ..... A61B 6/4291; A61B 6/484; A61B 6/4035; G21K 1/06; G21K 1/067
(Continued)

(56) References Cited

U.S. PATENT DOCUMENTS 5,812,629 A * 9/1998 Clauser ............................ 378/62
6,366,643 B1 * 4/2002 Davis et al. .................... 378/154
(Continued)

FOREIGN PATENT DOCUMENTS

EP           1731099      12/2006
WO       WO2011105306    9/2011

*Primary Examiner* — Allen C. Ho

(57) ABSTRACT

The present invention relates to differential phase-contrast imaging, in particular to a structure of a diffraction grating, e.g. an analyzer grating and a phase grating, for X-ray differential phase-contrast imaging. In order to provide enhanced phase-gradient based image data, a diffraction grating (14, 15) for X-ray differential phase-contrast imaging, is provided with a first sub-area (23) comprising at least one portion (24) of a first grating structure (26) and at least one portion (28) of a second grating structure (30). The first grating structure comprises a plurality of bars (34) and gaps (36) with a first grating orientation $G_{O1}$ (37), being arranged periodically, wherein the bars are arranged such that they change the phase and/or amplitude of an X-ray radiation and wherein the gaps are X-ray transparent. The second grating structure comprises a plurality of bars (40) and gaps (42) with a second grating orientation $G_{O2}$ (44), being arranged periodically, wherein the bars are arranged such that they change the phase and/or amplitude of an X-ray radiation and wherein the gaps are X-ray transparent. The first grating orientation $G_{O1}$ is different than the second grating orientation $G_{O2}$. Thus, phase-gradient based image information can be acquired for different directions without the necessity to rotate or pivot any of the respective gratings between the acquisition steps, for example.

23 Claims, 17 Drawing Sheets

(51) Int. Cl.
*G01N 23/04* (2006.01)
*A61B 6/03* (2006.01)
*G01N 23/20* (2006.01)
*A61B 6/06* (2006.01)

(52) U.S. Cl.
CPC ......... *A61B 6/4291* (2013.01); *G01N 23/046* (2013.01); *G01N 23/20075* (2013.01); *G21K 1/06* (2013.01); *G21K 1/067* (2013.01); *A61B 6/06* (2013.01)

(58) Field of Classification Search
USPC .............. 378/19, 36, 62, 147, 149, 154, 155
See application file for complete search history.

(56) References Cited

U.S. PATENT DOCUMENTS

| | | | | |
|---|---|---|---|---|
| 6,968,041 B2* | 11/2005 | Hoheisel et al. | ............. | 378/154 |
| 7,180,979 B2* | 2/2007 | Momose | ........................ | 378/62 |
| 7,433,444 B2* | 10/2008 | Baumann et al. | ............. | 378/62 |
| 7,492,871 B2* | 2/2009 | Popescu et al. | ............. | 378/145 |
| 7,522,698 B2* | 4/2009 | Popescu | ................ | A61B 6/032 |
| | | | | 378/19 |
| 7,522,708 B2* | 4/2009 | Heismann et al. | ........... | 378/145 |
| 7,535,986 B2* | 5/2009 | Hempel | ............ | A61B 5/02007 |
| | | | | 378/4 |
| 7,564,941 B2* | 7/2009 | Baumann et al. | ............. | 378/19 |
| 7,639,786 B2* | 12/2009 | Baumann et al. | ............. | 378/145 |
| 7,646,843 B2* | 1/2010 | Popescu et al. | .................. | 378/5 |
| 7,746,981 B2* | 6/2010 | Takahashi et al. | .......... | 378/98.8 |
| 7,817,777 B2* | 10/2010 | Baumann | ................ | A61B 6/00 |
| | | | | 378/36 |
| 7,889,838 B2* | 2/2011 | David et al. | ..................... | 378/36 |
| 7,924,973 B2* | 4/2011 | Kottler | ................ | G01B 15/025 |
| | | | | 378/36 |
| 7,945,018 B2* | 5/2011 | Heismann | ............. | A61B 6/032 |
| | | | | 378/145 |
| 7,949,095 B2* | 5/2011 | Ning et al. | ...................... | 378/62 |
| 7,983,381 B2* | 7/2011 | David | .................... | A61B 6/032 |
| | | | | 378/4 |
| 8,005,185 B2* | 8/2011 | Popescu | ......................... | 378/36 |
| 8,009,796 B2* | 8/2011 | Popescu | ................ | A61B 6/032 |
| | | | | 378/19 |
| 8,009,797 B2* | 8/2011 | Ouchi | .................. | G06T 7/0002 |
| | | | | 378/36 |
| 8,041,004 B2* | 10/2011 | David et al. | ..................... | 378/36 |
| 8,073,099 B2* | 12/2011 | Niu | .......................... | A61B 6/00 |
| | | | | 378/36 |
| 8,139,711 B2* | 3/2012 | Takahashi | ....................... | 378/36 |
| 8,165,270 B2* | 4/2012 | David | ........................ | G01T 1/00 |
| | | | | 378/145 |
| 8,184,771 B2* | 5/2012 | Murakoshi et al. | ............ | 378/62 |
| 8,223,924 B2* | 7/2012 | Borner et al. | ................. | 378/145 |
| 8,243,879 B2* | 8/2012 | Itoh | ......................... | G21K 1/025 |
| | | | | 359/238 |
| 8,280,000 B2* | 10/2012 | Takahashi | ....................... | 378/62 |
| 8,351,570 B2* | 1/2013 | Nakamura | ................ | G21K 1/06 |
| | | | | 378/145 |
| 8,374,309 B2* | 2/2013 | Donath et al. | .................. | 378/19 |
| 8,411,816 B2* | 4/2013 | Ohara | ..................... | A61B 6/484 |
| | | | | 378/36 |
| 8,451,975 B2* | 5/2013 | Tada | ..................... | A61B 6/4291 |
| | | | | 378/207 |
| 8,532,252 B2* | 9/2013 | Nakamura | ............... | G21K 1/06 |
| | | | | 378/145 |
| 8,559,594 B2* | 10/2013 | Ouchi | ..................... | G01N 23/04 |
| | | | | 378/36 |
| 8,565,371 B2* | 10/2013 | Bredno | .................. | A61B 6/032 |
| | | | | 378/9 |
| 8,576,983 B2* | 11/2013 | Baeumer | ..................... | G21K 1/06 |
| | | | | 378/145 |
| 8,591,108 B2* | 11/2013 | Tada | ........................ | A61B 6/00 |
| | | | | 378/207 |
| 8,632,247 B2* | 1/2014 | Ishii | .............................. | 378/207 |
| 8,718,228 B2* | 5/2014 | Nakamura | ............... | A61B 6/06 |
| | | | | 378/149 |
| 8,755,487 B2* | 6/2014 | Kaneko | ..................... | A61B 6/06 |
| | | | | 378/36 |
| 8,781,069 B2* | 7/2014 | Murakoshi | ........... | A61B 6/4233 |
| | | | | 378/36 |
| 8,824,629 B2* | 9/2014 | Ishii | .............................. | 378/62 |
| 8,831,174 B2* | 9/2014 | Kohara et al. | .................. | 378/62 |
| 8,848,863 B2* | 9/2014 | Schusser et al. | ............... | 378/16 |
| 8,855,265 B2* | 10/2014 | Engel et al. | ..................... | 378/62 |
| 8,903,042 B2* | 12/2014 | Ishii | ..................... | A61B 6/4233 |
| | | | | 378/207 |
| 8,908,274 B2* | 12/2014 | Teshima | .................... | G21K 1/06 |
| | | | | 359/563 |
| 8,989,353 B2* | 3/2015 | Kaneko | .................. | G21K 1/025 |
| | | | | 378/145 |
| 8,989,474 B2* | 3/2015 | Kido | .................... | A61B 6/4291 |
| | | | | 382/132 |
| 8,995,613 B2* | 3/2015 | Ouchi | .................. | G01N 23/046 |
| | | | | 378/62 |
| 9,001,969 B2* | 4/2015 | Murakoshi | ........... | A61B 6/4233 |
| | | | | 378/70 |
| 9,006,656 B2* | 4/2015 | Itoh | ........................ | G01N 23/04 |
| | | | | 250/336.1 |
| 9,036,773 B2* | 5/2015 | David | .................. | A61B 6/4035 |
| | | | | 378/36 |
| 9,046,466 B2* | 6/2015 | Ouchi | .................... | A61B 6/484 |
| 9,066,649 B2* | 6/2015 | Roessl | ..................... | A61B 6/00 |
| 9,066,704 B2* | 6/2015 | Den | .................... | G01N 23/046 |
| 9,084,528 B2* | 7/2015 | Geller | ..................... | A61B 6/00 |
| 9,105,369 B2* | 8/2015 | Koehler | .................... | A61B 6/032 |
| 9,107,637 B2* | 8/2015 | Ouchi | ..................... | A61B 6/06 |
| 9,287,017 B2* | 3/2016 | Koehler | ................... | G21K 1/06 |
| 9,364,191 B2* | 6/2016 | Ning | ....................... | A61B 6/032 |
| 9,538,970 B2* | 1/2017 | Koehler | .................... | A61B 6/482 |
| 9,597,050 B2* | 3/2017 | Roessl | ..................... | A61B 6/484 |
| 2007/0183583 A1 | 8/2007 | Baumann | | |
| 2008/0065340 A1 | 3/2008 | Otsuki | | |
| 2013/0208864 A1* | 8/2013 | Rossl | ..................... | A61B 6/484 |
| | | | | 378/62 |
| 2015/0187096 A1 | 7/2015 | Baturin | | |
| 2015/0216499 A1 | 8/2015 | Martens | | |

* cited by examiner

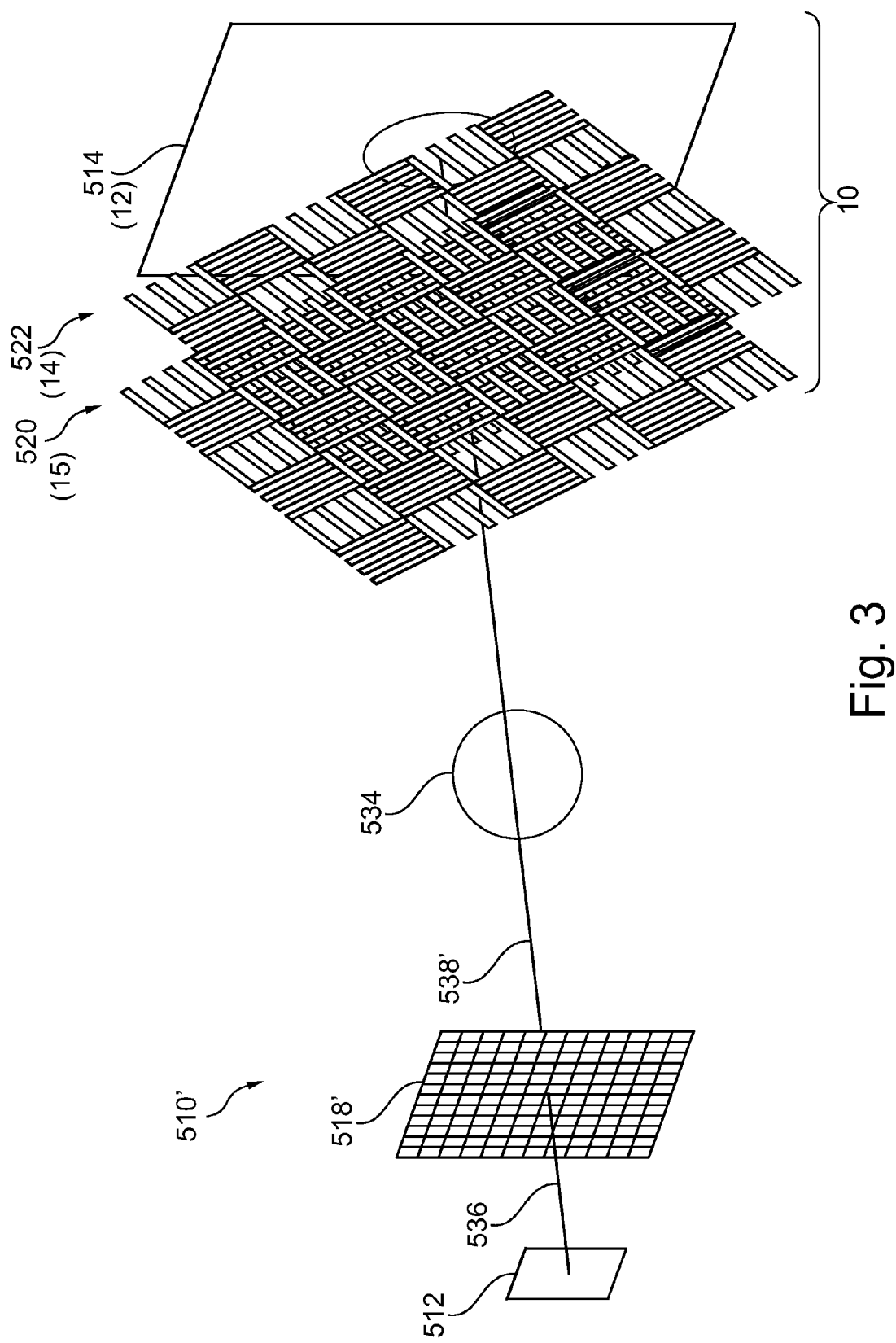

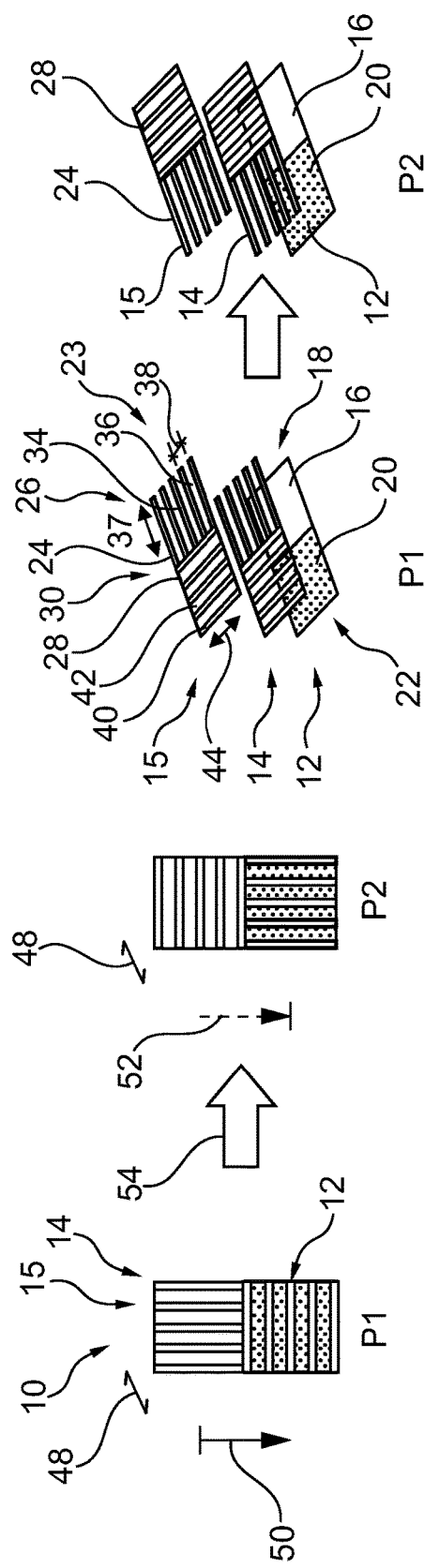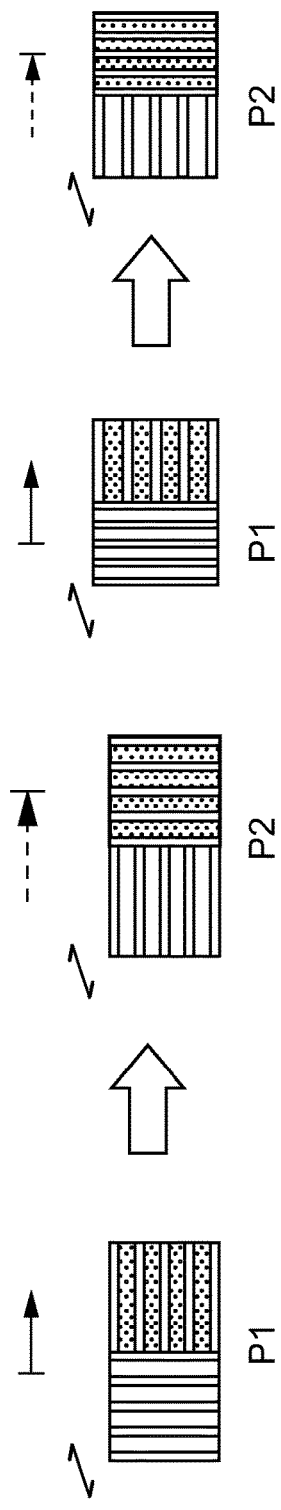

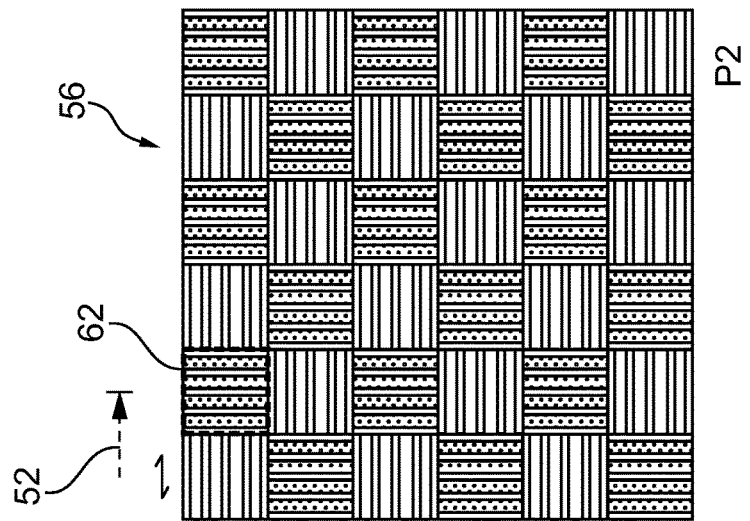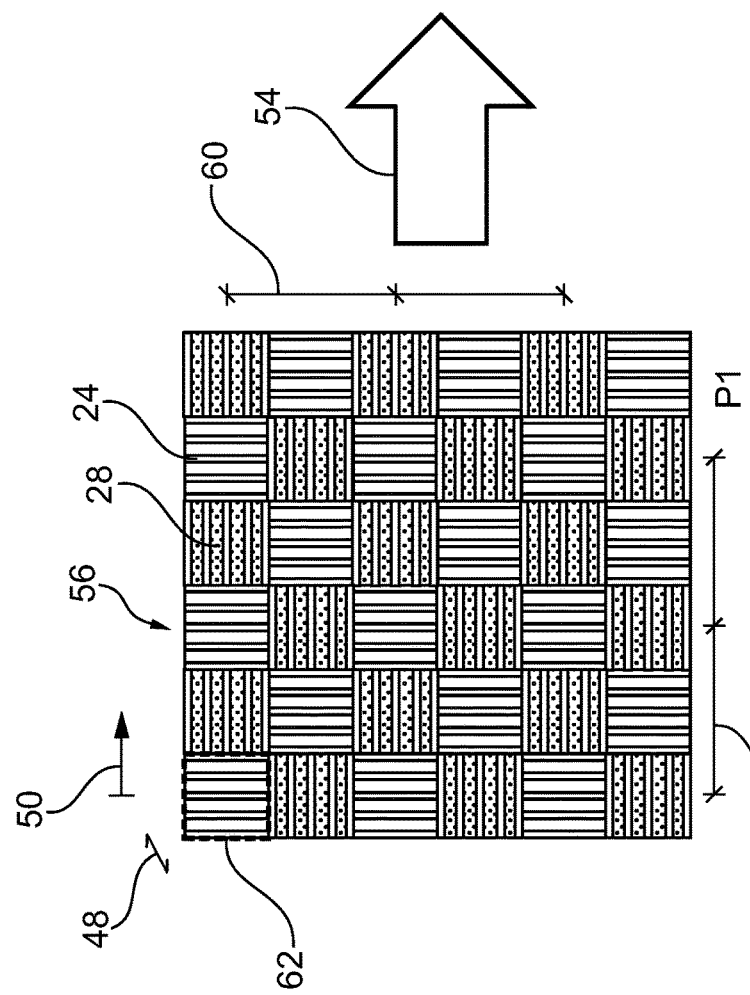
Fig.7b
Fig.7a

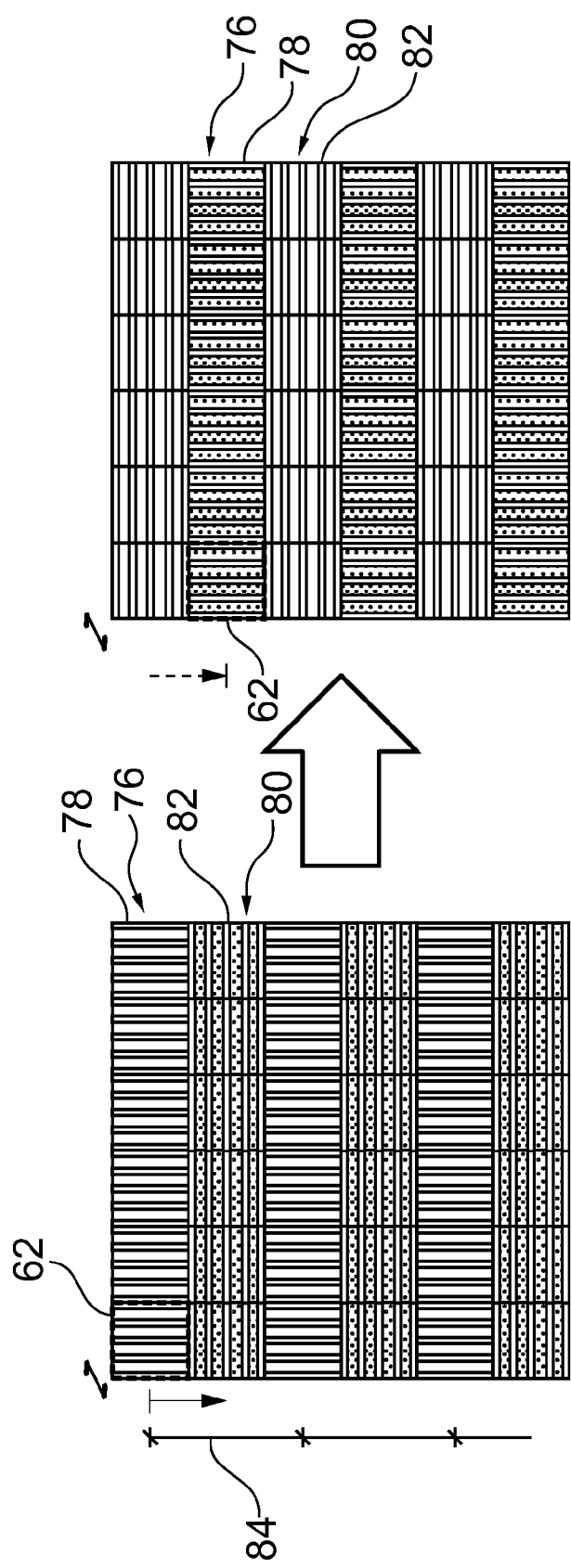

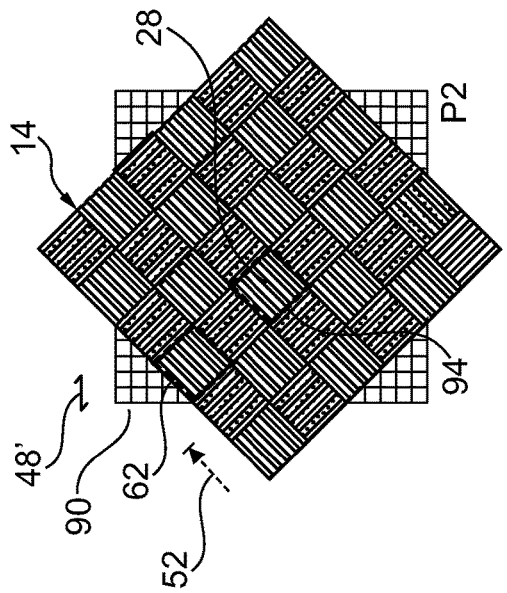
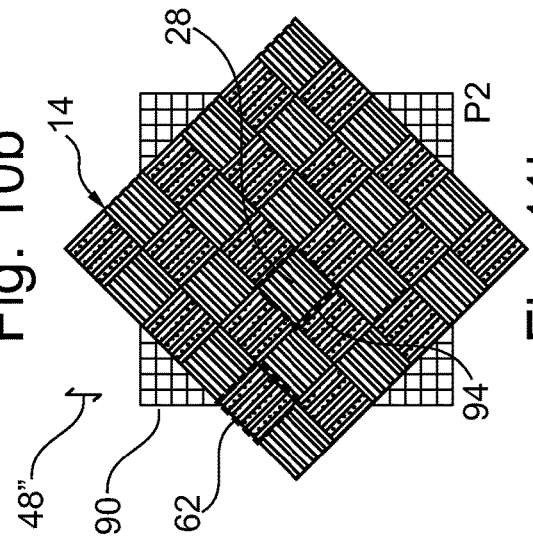
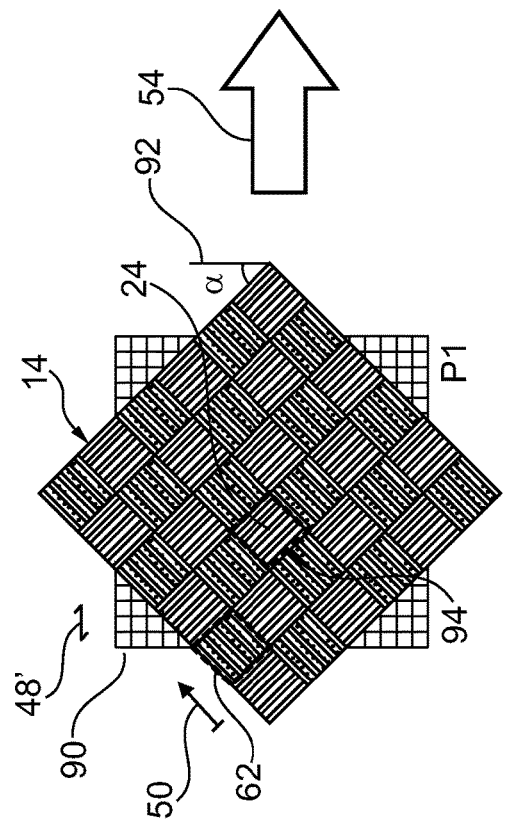
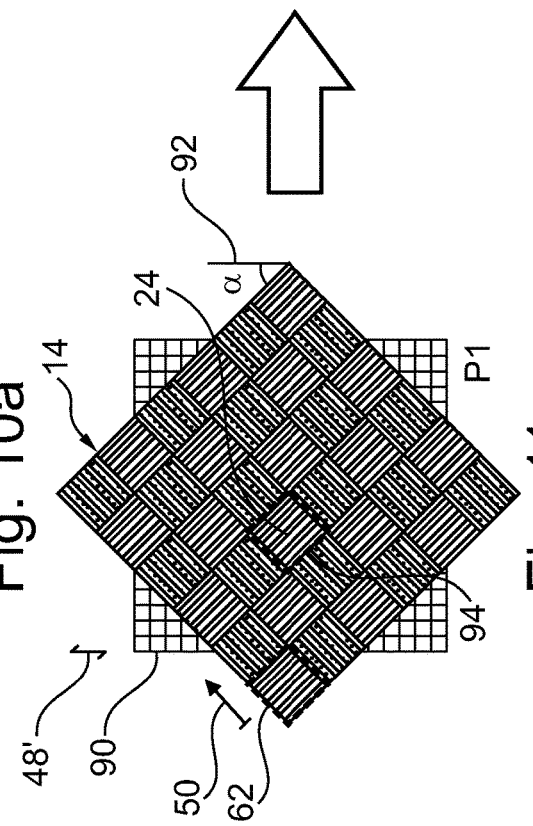

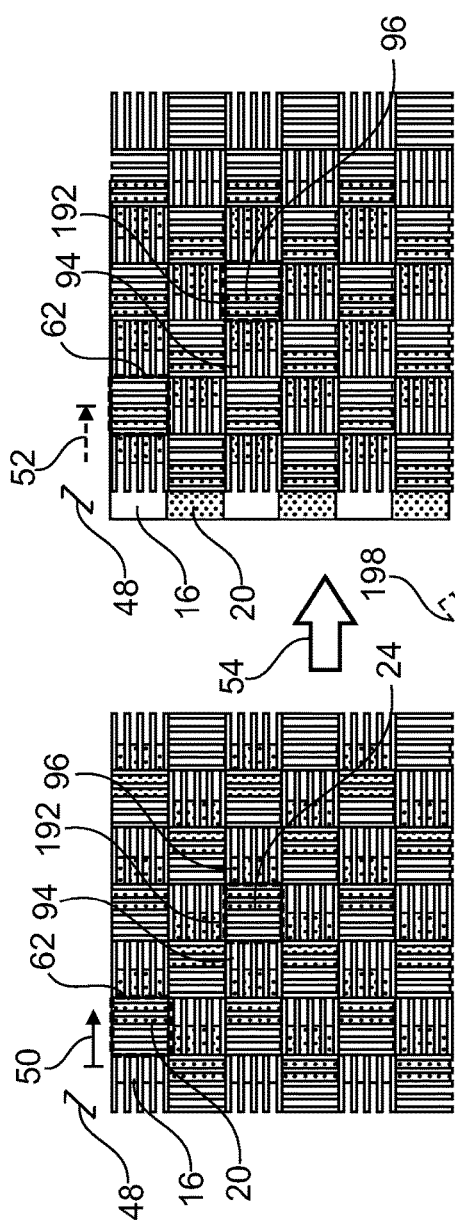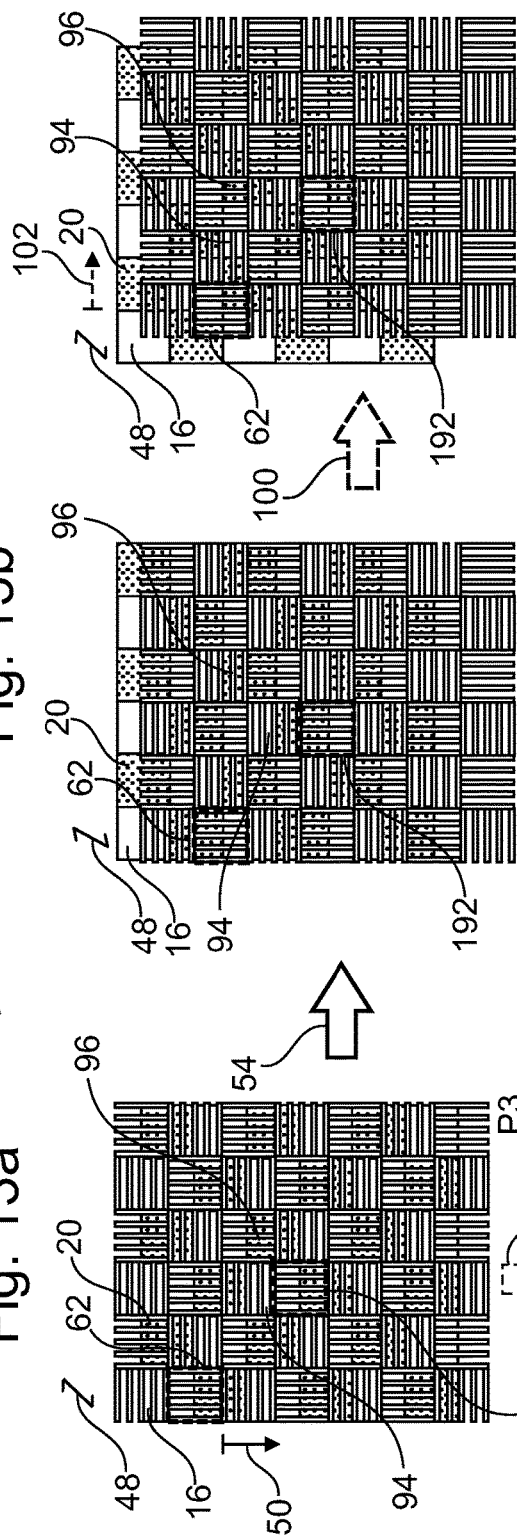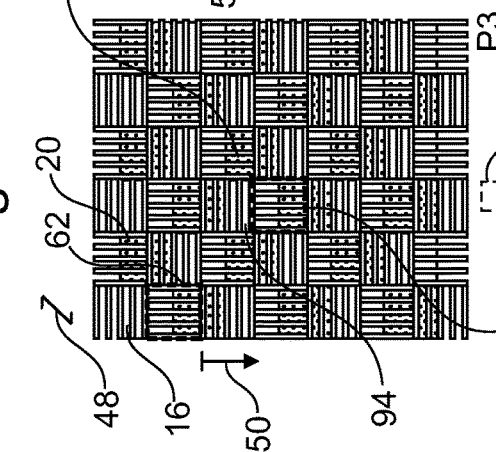

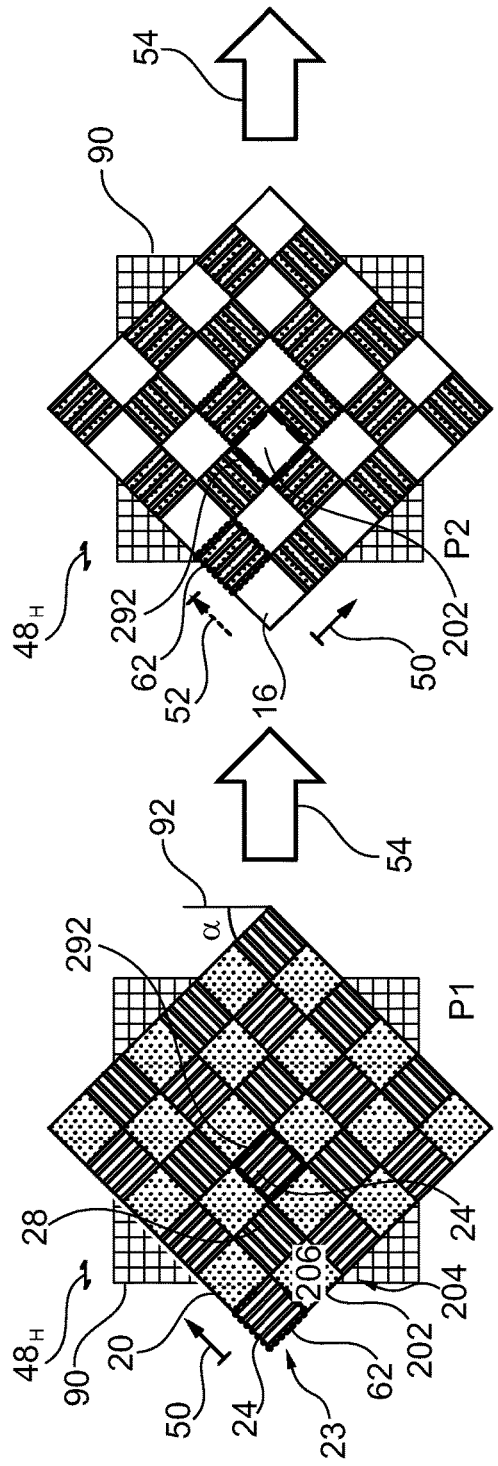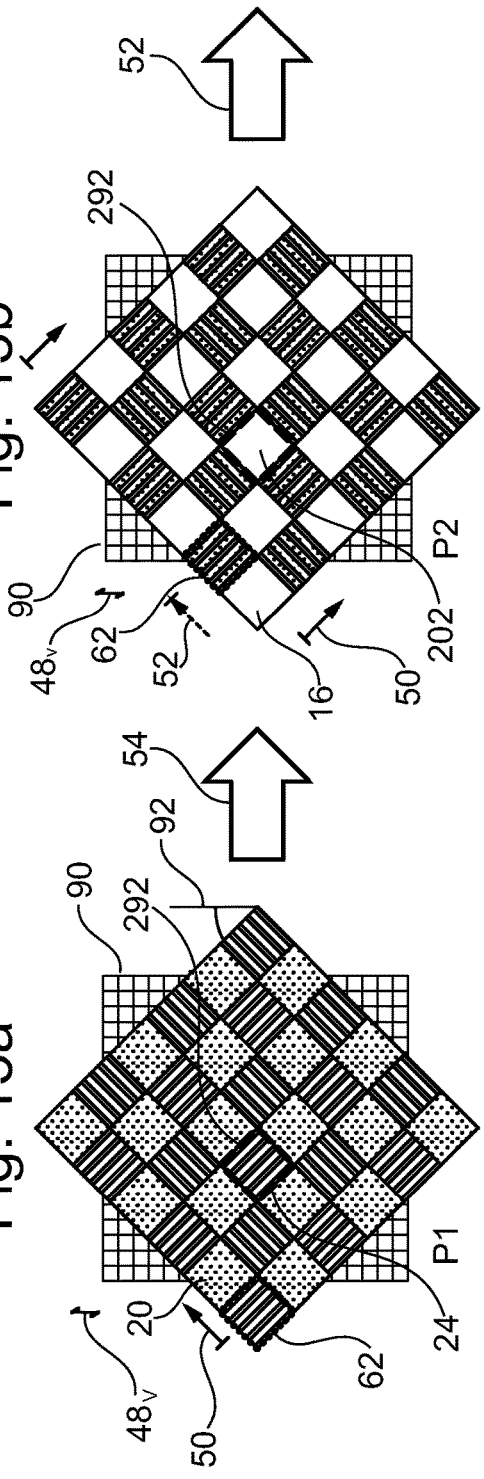

DIFFERENTIAL PHASE-CONTRAST IMAGING

FIELD OF THE INVENTION

The present invention relates to differential phase-contrast imaging, in particular to diffraction gratings for X-ray differential phase-contrast imaging, a detector arrangement of an X-ray system for generating phase-contrast images of an object, an X-ray image acquisition device for generating phase-contrast images of an object, a medical X-ray imaging system for differential phase-contrast imaging, a method for differential phase-contrast imaging as well as a computer program element and a computer-readable medium.

BACKGROUND OF THE INVENTION

Differential phase-contrast imaging is used, for example, to enhance the contrast of low absorbing specimen, compared to conventional amplitude contrast images. In EP 1 731 099 A1, an X-ray interferometer arrangement is described comprising a standard polychromatic X-ray source, a source grating, a beam splitter grating and an analyzer grating and an image detector. An object is arranged between the source grating and the beam splitter grating, i.e. the phase grating. By phase stepping the analyzer grating it is possible to record raw image data comprising phase information. The gratings, for example the phase grating and the analyzer grating, comprise a plurality of X-ray transparent slits between trenches of absorbing material, for example gold.

SUMMARY OF THE INVENTION

It has been shown that the phase-gradient based information is only achieved in one grating direction.

Hence, there may be a need to provide enhanced phase-gradient based image data.

The object of the present invention is solved by the subject matter of the independent claims, wherein further embodiments are incorporated in the dependent claims.

It should be noted that the following described aspects of the invention apply also for the diffraction grating, the detector arrangement, the X-ray image acquisition device, the medical X-ray imaging system, the method, the computer program and the computer readable medium.

According to an exemplary embodiment of the invention, a diffraction grating for X-ray differential phase contrast imaging is provided, comprising a first sub-area with at least one portion of a first grating structure and at least one portion of a second grating structure. The first grating structure comprises a plurality of bars and gaps with a first grating orientation $G_{O1}$, being arranged periodically. The bars are arranged such that they change the phase and/or amplitude of an X-ray radiation and the gaps are X-ray transparent. The second grating structure comprises a plurality of bars and gaps with a second grating orientation $G_{O2}$, being arranged periodically. The bars are arranged such that they change the phase and/or amplitude of an X-ray radiation and the gaps are X-ray transparent. The first grating orientation $G_{O1}$ is different than the second grating orientation $G_{O2}$.

According to the present invention, the term "changing phase" relates to shifting the phase of the X-ray radiation.

According to the present invention, the term "X-ray transparent" relates to the fact that X-ray radiation passing the grating is not changed in its phase, i.e. it is not phase shifted, and not changed in its amplitude, both to a measurable or reasonable amount.

According to a further exemplary embodiment, the first grating orientation $G_{O1}$ is arranged transverse to the second grating orientation $G_{O2}$, for example in 90°.

According to a further aspect of the invention, the plurality of bars and gaps of the first grating structure are arranged periodically with a first grating pitch $P_{G1}$, and the bars and gaps of the second grating structure are arranged periodically with a second grating pitch $P_{G2}$.

According to a further aspect of the invention, the first and second pitches $P_{G1}$ and $P_{G2}$ are equal.

According to a further exemplary embodiment, the portions of the first and second grating structures are arranged across the area of the diffraction grating in a chess-board pattern.

According to a further exemplary embodiment, at least one portion of a second sub-area is provided; wherein the second sub-area is X-ray transparent and wherein the at least one portion of the second sub-area provides an X-ray transparent aperture in the grating. The portions of the first and second sub-areas are arranged in an alternating manner in at least one direction.

According to a further exemplary embodiment, a detector arrangement of an X-ray system for generating phase-contrast images of an object is provided, comprising a first diffraction grating, a second diffraction grating, and a detector with a sensor. The sensor comprises at least one sensor pixel of a first sub-group of pixels and at least one sensor pixel of a second sub-group of pixels. The first diffraction grating is a phase grating and the second diffraction grating is an analyzer grating. The phase grating and the analyzer grating are provided as a diffraction grating for X-ray differential phase-contrast imaging according to one of the above-mentioned embodiments. The analyzer grating and/or the phase grating are adapted to be stepped in a predetermined relation to analyzer grating. The first and second diffraction gratings are each adapted to be translated in relation to the sensor from a first position (P1) to at least a second position (P2) with a first translation pitch $P_{T1}$. The translation pitch $P_{T1}$ is adapted to the portions of the first and/or second grating structures of the diffraction gratings. In the first and second position, different fractions of the sensor are arranged behind the portions of the first and second grating structures.

According to a further exemplary embodiment, the first and/or second diffraction gratings are adapted to be phase-stepped in an acute angle α to the first and/or second grating structure.

For example, the phase-stepping direction is arranged in an angle of 45° to the first and/or second grating structure.

According to a further embodiment, the acute angle is 30° or 60°, i.e., in case of orthogonally arranged first and second grating directions, the angle to the first and second grating structure is different for each grating structure direction.

According to a further exemplary embodiment, an X-ray image acquisition device for generating phase-contrast images of an object is provided, with an X-ray source, a source grating, a phase grating, an analyzer grating, and a detector. The X-ray source generates an X-ray beam of polychromatic spectrum of X-rays, wherein the source grating is adapted to provide sufficient transverse coherence to illuminate at least one full grating pitch of the phase grating coherently, so that interference can be observed at the location of the analyzer grating. The phase grating is illuminated by several of the slits and can be called a beam
} splitter grating as well as it splits the beam in the two leading orders, i.e. 1$^{st}$ orders of diffraction, as the 0$^{th}$ order is cancelled out exactly.

The phase grating, the analyzer grating and the detector are provided as a detector arrangement according to one of the above-mentioned embodiments.

According to a further exemplary embodiment, a medical X-ray imaging system for differential phase contrast imaging is provided, with an X-ray image acquisition device for generating phase-contrast images of an object, according to the embodiment described above, a processing unit, an interface unit, and an object-receiving device. The processing unit is adapted to control the X-ray source as well as the phase-stepping of the analyzer grating and the translation of the phase grating and the analyzer grating. The interface unit is adapted to provide the recorded first and second raw image data to the processing unit. The object-receiving device is adapted to receive the object of interest for the phase contrast image acquisition.

According to a further exemplary embodiment, a method for differential phase for differential phase contrast imaging is provided, comprising the following steps:

aa1) Applying coherent X-ray radiation to an interferometer with two diffraction gratings in a first position (P1), which diffraction gratings each comprise at least two parts with different grating orientations, wherein a first diffraction grating is a phase grating and a second diffraction grating is an analyzer grating.

aa2) Phase-stepping the analyzer grating.

aa3) Recording first raw image data with a sensor with at least two parts, wherein a first and a second part are recording phase contrast image information relating to the first and the second grating orientations.

b) Translating the analyzer grating and the phase grating to a second position (P2).

cc1) Applying coherent X-ray radiation to the interferometer in the second position.

cc2) Phase-stepping the analyzer grating.

cc3) Recording second raw image data with the sensor; wherein the first and the second part are recording phase contrast image information relating to the second and the first grating orientations.

d) Providing the recorded first and second raw image data as raw image data.

It can be seen as the gist of the invention to provide a diffraction grating with a grating structure having different grating orientations in different parts of a grating area. Thus, phase-gradient based image information can be acquired for different directions without the necessity to rotate or pivot any of the respective gratings between the acquisition steps, for example. Following, enhanced image information can thus be acquired and provided.

These and other aspects of the present invention will become apparent from and elucidated with reference to the exemplary embodiments described hereinafter.

BRIEF DESCRIPTION OF THE DRAWINGS

Exemplary embodiments of the drawings will be described in the following with reference to the following drawings.

FIG. 3 schematically shows a further exemplary embodiment of an X-ray image acquisition device for generating phase contrast images according to the invention.

FIGS. 4a and 4b schematically show a detector arrangement with a diffraction grating according to the invention.

FIGS. 5 to 6 show further exemplary embodiments of the detector arrangement of FIG. 3.

FIGS. 7a, 7b, 8a, 9b, 9a, and 9b show further exemplary embodiments of detector arrangement according to the invention.

FIGS. 10a, 10b, 11b, and 12a-12d show further exemplary embodiments of detector arrangements according to the invention.

FIGS. 13a-13f show a further exemplary embodiment of a detector arrangement according to the invention.

FIGS. 15a-15d and 16a-16d show a further exemplary embodiment of a detector arrangement according to the invention.

DETAILED DESCRIPTION OF EMBODIMENTS

Figure 1:
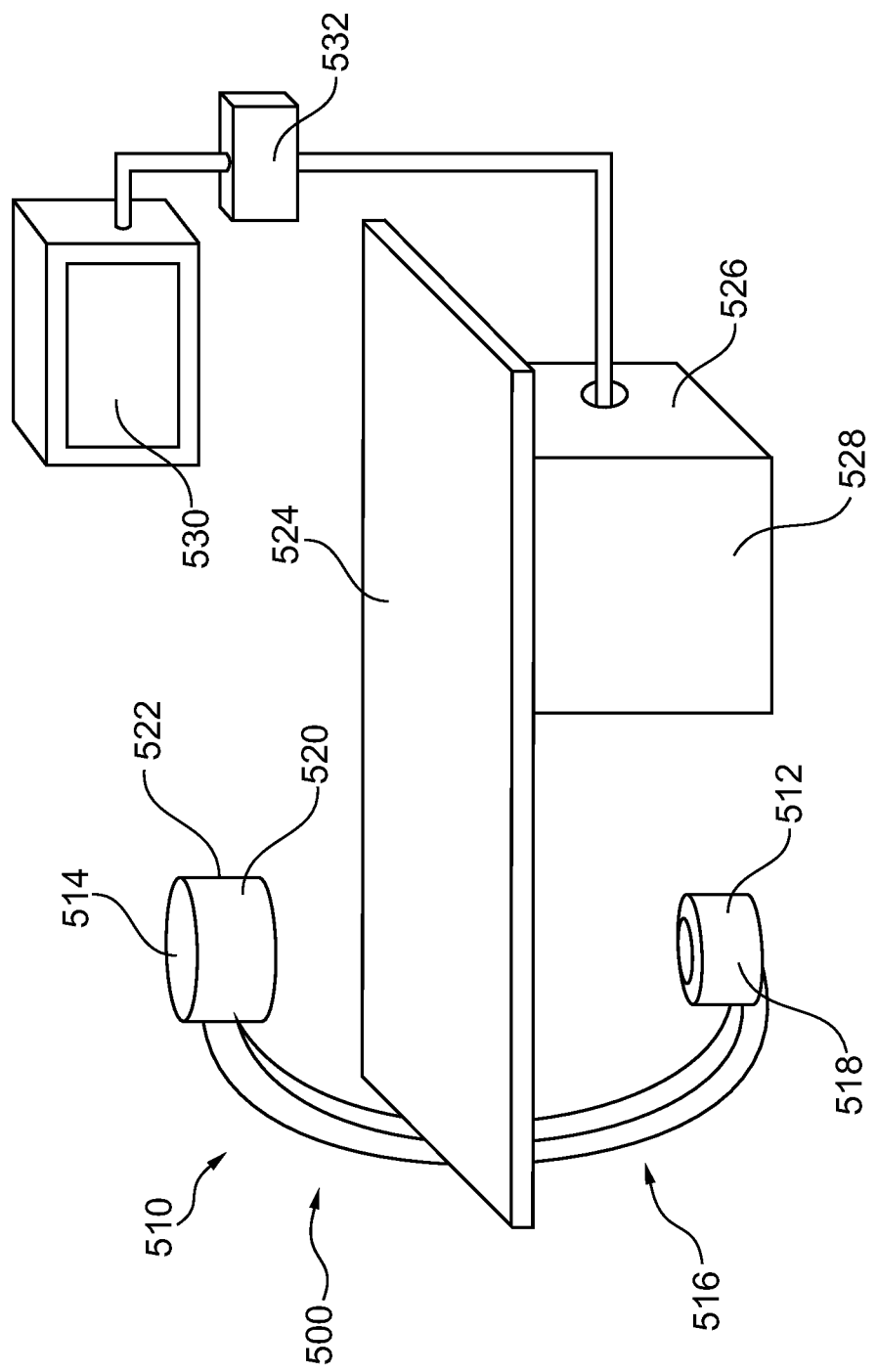
FIG. 1 schematically shows an example of a medical X-ray imaging system according to the invention.

In FIG. 1, a medical imaging system 500 for differential phase contrast imaging according to the invention is schematically shown. An X-ray image acquisition device 510 for generating phase contrast images of an object, for example a patient, is shown as part of the medical imaging system 500. The X-ray image acquisition device 510 comprises an X-ray source 512 as well as a detector 514, which is arranged opposite to the X-ray source 512, for example on a C-arm structure 516. Further, the X-ray image acquisition device 510 comprises a source grating which is not shown, a phase grating 520 and an analyzer grating 522 (also not shown). For a more detailed description of these aspects, see below.

As an object-receiving device, a table 524 is provided which is arranged at least partially between the X-ray source 512 and the detector 514.

Further, a processing unit 526 and an interface unit 528 are provided. Furthermore, a display device 530 is shown above the table 524 to display information. Further, for input by the user, an interaction panel, indicated with reference numeral 532, is provided.

The example shown is of a so-called C-type X-ray image acquisition device having an arm in form of a C. The image detector 514 is arranged at the one end of the C-arm 516 and the source 512 of X-ray radiation is located at the opposite end of the C-arm 516. The arm itself can be movably mounted and thus be rotated around the object of interest. Simply said, it is possible to acquire images for different viewing directions. However, it must be noted that, of course, other forms of X-ray image acquisition devices are also possible, for example a gantry with a rotating pair of X-ray source and detector.

According to an aspect of the invention, the processing unit 526 is adapted to control the X-ray source 512 and the phase-stepping of the analyzer grating. The processing unit 526 is also adapted to control the translating of the phase grating and the analyzer grating, which will be explained further below.

According to an aspect of the invention, the processing unit 526 is adapted to control the phase-stepping of the phase grating 520.

The interface unit 528 is arranged such that recorded data, which is recorded by the detector 514, can be provided to the processing unit 526.

In the following, the X-ray image acquisition device 510 will now be described with reference to FIG. 2.

The X-ray image acquisition device 510 for generating phase contrast images comprises the X-ray source 512, indicated by a simple square, the source grating 518, the phase grating 520, the analyzer grating 522, and the detector 514 for examination of an object. The object is indicated with reference numeral 534. Further, an X-ray beam 536 of polychromatic spectrum X-rays is provided by the X-ray source 512, which is provided, for example, as a conventional X-ray source. The X-ray radiation beam 536 is applied to the source grating 518. The source grating 518, also referred to as G0, is adapted to provide sufficient transverse coherence to illuminate at least one full grating pitch of the phase grating 520 coherently, so that interference can be observed at the location of the analyzer grating 522. Simply said, the source grating 518 is "splitting" the X-ray radiation 536 such that coherent X-ray radiation is provided (not further shown).

Figure 2:
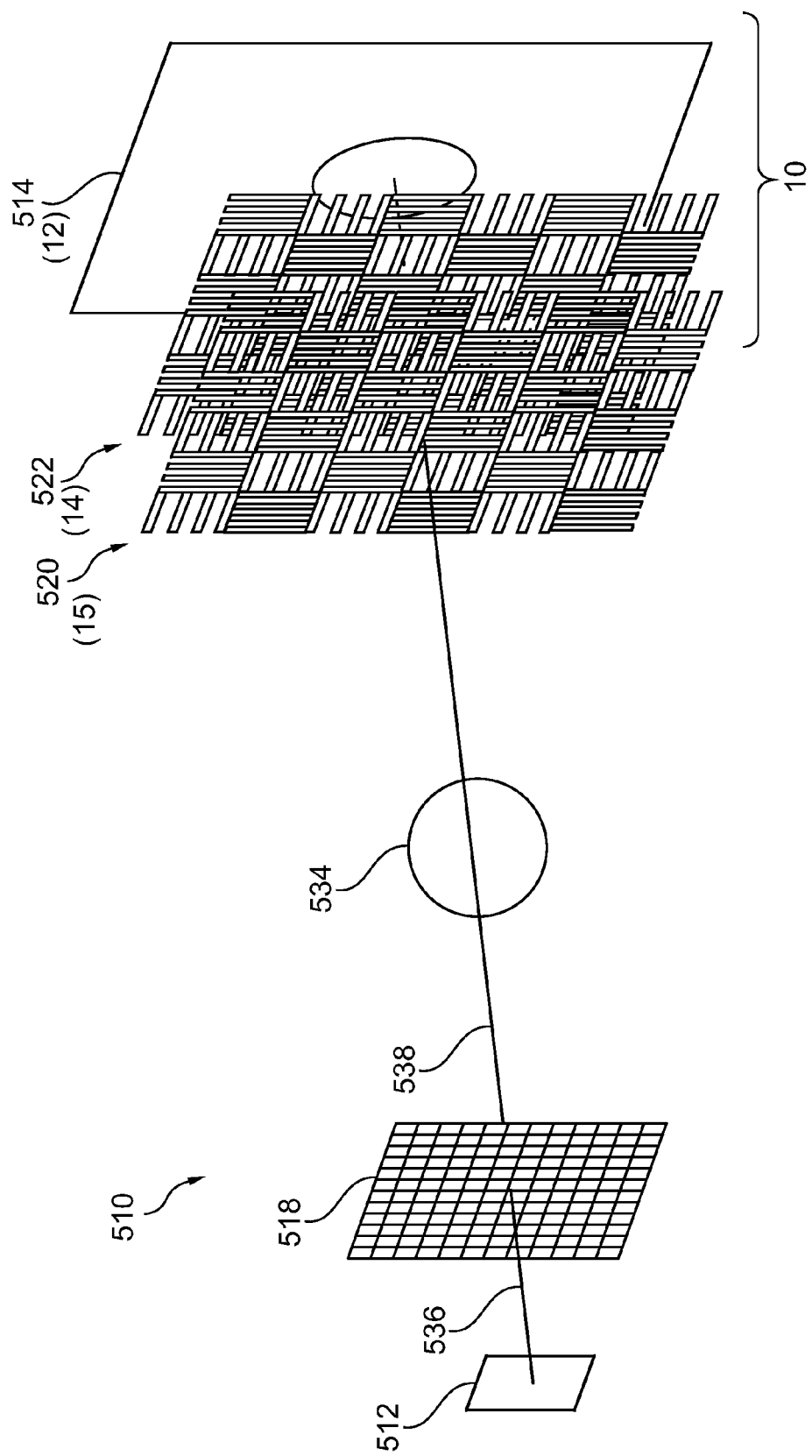
FIG. 2 schematically shows an X-ray image acquisition device for generating phase contrast images according to the invention.

For example, in FIG. 2, the source grating 518 provides a coherent radiation, which has high transversal coherence in two directions.

Of course, instead of the source grating 518 and the source 512, provided as a conventional X-ray source, a microfocus tube or microfocus tube arrangement, e.g. an array, can be provided.

According to a further example, for the coherent X-ray radiation, a plurality of nano-tubes is provided in order to generate a respective plurality of X-ray beams.

The X-ray beam passing the source grating 518 is indicated with reference numeral 538. The phase grating 520 is illuminated by several of the slits and can be called a beam splitter grating as well as it splits the beam in the two leading orders, i.e. $1^{st}$ orders of diffraction, as the $0^{th}$ order is cancelled out exactly. After recombining the split beams behind the phase grating 520, the recombined beam is applied to the analyzer grating 522. Then, the detector 514 with the sensor, not further shown, records raw image data while analyzer grating 522 is phase-stepped which will be explained further below.

The phase grating 520, the analyzer grating 522, and the detector 514 are provided as a detector arrangement 10 according to the invention, which will be described in the following.

Further, the phase grating 520 and the analyzer grating 522 are provided as a diffraction grating for X-ray differential phase contrast imaging according to one of the embodiments described below.

According to an exemplary embodiment, the analyzer grating 522 is adapted to be B stepped transversely over at least one period of the analyzer grating 522. Further, the phase grating 520 and the analyzer grating 522 are provided as a diffraction grating for X-ray differential phase-contrast imaging according to one of the embodiments described below. According to a further aspect, also the phase grating 520, also referred to as G1, is stepped with respect to the analyzer grating 522, referred to as G2. Then however, it suffices to step the phase grating 520 by only ½ of its pitch, as the frequency of the interference fringes at the analyzer grating 522 is double the pitch of G1, i.e., the phase grating, which is the case for parallel beams. For cone beams, a magnification leads to a slight deviation from the factor 2.

In FIG. 3, a further exemplary embodiment of an X-ray image acquisition device 510' is schematically shown. As can be seen, a source grating 518' is provided, thus providing a splitted beam 538' with coherence in two directions. As the source grating 518', a grid-like structure is shown indicating the transversal coherence in two directions. Further, the phase grating 520, also indicated with reference numeral 15, and the analyzer grating 522, also indicated with reference numeral 14, are arranged in an acute angle to the coherence of the splitted beam 538'. As an example, the phase grating and the analyzer grating are rotated by an angle of 45°.

According to a further embodiment, although not shown, x-ray beams with transverse coherence in only one direction are provided, e.g. by providing a source grating with linear grating or one or several line sources instead of the grid-like source grating.

A number of lines of the source grating 518' indicate the direction of the source grating trenches and thus, the transverse coherence of the x-rays is largely perpendicular to the lines.

Of course, it is also possible to generate x-ray beams with the transverse coherence in the direction perpendicular to the one shown in the figure According to one aspect, one line source is provided.

According to one aspect, several line sources are provided.

According to a further aspect, a small focus is provided, e.g. a microfocus tube.

In FIGS. 4a and 4b, the detector arrangement 10 of an X-ray system for generating phase contrast images of an object is schematically shown. The detector arrangement 10 comprises a detector 12 with a sensor and a first and second diffraction grating, which are provided as an analyzer grating 14 and a phase grating 15. FIG. 4a shows a plan view, and FIG. 4b shows an isometric view, in a so-called exploding illustration.

With relation to the direction of radiation to be applied, the phase grating 15 and the analyzer grating 14 are arranged in front of the detector 12, according to the following figures, wherein the phase grating 15 is arranged in front of the analyzer grating 14.

In FIG. 4, the analyzer grating 14 is arranged above the detector, and the phase grating 15 is arranged above the analyzer grating 14. For a better understanding, FIG. 4b shows the perspective view of the schematic arrangement.

It is explicitly noted that in the following, the analyzer grating 14 is described. However, according to the present invention, the grating features of analyzer grating 14 are also provided for the phase grating 15. Further, the phase grating 15 and the analyzer grating 14 are arranged in front of each other with the same grating structure according to one of the embodiments described for the analyzer grating, in order to provide the detection of phase-gradient information.

In other words, the features and characteristics described for the analyzer grating 14 also apply to the phase grating 15, which is not further shown for a better understanding of the drawings.

According to a further aspect, the bars of the analyzer grating are X-ray absorbing such that they are changing the amplitude of X-ray radiation passing the grating.

According to a further exemplary embodiment, the bars of the phase grating are changing the phase of X-ray radiation passing the grating.

As can be seen, the sensor of the detector 12 comprises at least one sensor pixel 16 of a first sub-group of pixels 18, and at least one sensor pixel 20 of a second sub-group of pixels 22 (see also below). The diffraction gratings 14, 15 for X-ray differential phase contrast imaging each comprise a first sub-area 23 with at least one portion 24 of a first grating structure 26 and at least one portion 28 of a second grating structure 30.

The first grating structure 26 comprises a plurality of bars 34 and gaps 36 with a first grating orientation $G_{O1}$ 37, being arranged periodically. The bars are arranged such that they change the phase and/or amplitude of an X-ray radiation, and the gaps are X-ray transparent.

According to an aspect of the invention, the bars of the analyzer grating 14 are X-ray absorbing such that they are changing the amplitude of X-ray radiation passing the grating.

According to an aspect of the invention, the bars of the phase grating 15 are changing the phase of X-ray radiation passing the grating.

According to another aspect, the source grating is provided as an absorption grating as well, since the Talbot is observable here, too.

The second grating structure 30 comprises a plurality of bars 40 and gaps 42 with a second orientation $G_{O2}$ 44, being arranged periodically. The bars 40 are X-ray absorbing, and the gaps 42 are X-ray transparent.

The first grating orientation $G_{O1}$ 37 is different than the second grating orientation $G_{O2}$.

According to an aspect of the invention, the plurality of the bars 34 and gaps 36 of the first grating structure 26 are arranged periodically with a first grating pitch $P_{G1}$ 38.

According to an aspect of the invention, the plurality of the bars 40 and gaps 42 of the second grating structure 30 are arranged periodically with a second grating pitch $P_{G2}$ 46.

According to a further aspect, the first and second grating pitches $P_{G1}$ and $P_{G2}$ are equal.

According to a further aspect (not shown), the first and second grating pitches $P_{G1}$ and $P_{G2}$ are different.

In case the first and second gratings pitch are different, it has to be taken into account that the Talbot distances for the first grating orientation and the second grating orientation have to equal, as the difference between phase-, and analyzer gratings has to be fixed. As the Talbot distances depend on the design energy, the pitch and the Talbot order, this requirement translates into a use of different design energies and/or Talbot orders for the first and the second grating orientation, respectively.

The analyzer grating 14 is adapted to be stepped in a predetermined relation to the analyzer grating 14.

According to an aspect of the invention, the analyzer grating 14 is adapted to be stepped in a predetermined relation to the first and/or second grating pitch $P_{G1}$, $P_{G2}$ of the analyzer grating 14.

In the example shown, the phase-stepping is indicated with a double arrow, with reference numeral 48. For example, the phase-stepping direction is having an angle of 45° with relation to both the first and the second grating orientations 37 and 44.

According to a further aspect, the phase grating 15 is adapted to be stepped in a predetermined relation to the analyzer grating 14.

According to a still further aspect, the phase grating 15 is adapted to be stepped in a predetermined relation to the first and/or second grating pitch $P_{G1}$, $P_{G2}$ of the analyzer grating 14.

The first and second diffraction gratings, i.e. the phase grating 15 and the analyzer grating 14, are adapted to be translated in relation to the sensor from a first position P1 shown in the left half of FIG. 4a to at least a second position P2 shown in the right half of FIG. 4a with a first translation pitch $P_{T1}$ which is indicated with arrows 50 and 52. The translation step is also indicated with a broad arrow 54.

It is noted that the arrow 50 is indicating a translation step to be performed and the arrow 52 is indicating a preceding translation step, i.e. a translation step which has been performed. These arrows are used throughout the following Figures and will thus not be explicitly mentioned at all instances where this is shown in the drawings. However, it is noted that these symbols are shown and explained in such a clear manner that they are clear to a skilled person and thus, they need no further explanation in the written description. The same applies to the broad arrow 54 indicating a translation step.

In FIG. 4b, the translation from the first position P1 to the second position P2 is shown in the perspective view.

Of course, all Figures are not shown in scale. Especially the grating structures and the distances of the gratings in the perspective illustrations are only shown schematically.

As can be seen in FIGS. 4a and 4b, the translation pitch $P_{T1}$ is adapted to the portions of the first and/or second grating structures of the diffraction gratings.

Further, in the first and second position, different fractions of the sensor are arranged behind the portions of the first and second grating structures. In FIG. 4a, in the left part, the sensor pixel 16 of the first sub-group of pixels is arranged below the portion 24 of the first grating structure 26. Further, the pixel 20 of the second sub-group of pixels 22 is arranged below the portion 28 of the second grating structure 30. After translating the gratings, which is shown in the right half of FIG. 4a, the pixel 16 of the first sub-group 18 of pixels is arranged below the portion 28 of the second grating structure 30, and the pixel 20 of the second sub-group of pixels 22 is arranged below the portion 24 of the first grating structure 26.

As can be seen in FIG. 5, according to a further aspect of the invention, the analyzer grating 14 and the detector 12 can be arranged such that translation occurs horizontal in the drawing, i.e. perpendicular to the first grating structure 26, whereas in FIG. 4, the translation occurs vertical, i.e. parallel to the first grating structure 26.

It must be noted that terms as "right", "left", "upwards" or "downwards" as well as "horizontal" and "vertical" relate to the page on which the figures are presented when looking at the pages in such a manner that the letters and numbers can be read, i.e. in most of the cases the figure pages are regarded in a landscape orientation.

As can be seen from FIG. 6, the portions of the first and second grating structures 26, 30 can be provided to be rectangular, wherein their extension in one direction differs from the extension in the second direction. Alternatively, as shown in FIGS. 4 and 5, the portions each have a square form.

According to a further aspect of the invention, the grating portions, i.e. the portions of the first grating structure and the portions of the second grating structure are provided in different shapes, such as triangular, hexagon, or others (not further shown).

As can be seen by these very schematic illustrations, with the analyzer grating 14 according to the invention, it is possible to acquire image data in a first step, wherein the first sub-group 18 of pixels records phase-gradient information in relation to a first grating orientation. The second sub-group of pixels 22 records phase-gradient based information with relation to the second grating orientation.

Due to the translation, indicated with the arrow 54, the analyzer grating 14 is then positioned such that the first sub-group of pixels 18 records phase-gradient based information with relation to the second grating orientation, and the second sub-group of pixels 22 records phase-gradient based information with relation to the first grating orientation.

According to a further aspect, in the first and/or second position, the at least one portion of the first or second grating structure is arranged partially in front of one of the first or second sub-group of pixels.

According to a further aspect of the invention, portions of the first and second grating structures 26, 30 are arranged in an alternating manner in a first and as second direction. For example, the first direction is referred to as the X direction and the second direction is the Y direction.

According to a further aspect, the relativity of the portions of the first grating structure is arranged in the X direction with a first X repetition pitch $P_{R1X}$.

According to a further aspect, a plurality of portions of the first grating structure is arranged in the Y direction, with a first Y repetition pitch $P_{R1Y}$.

According to a further aspect, a plurality of the portions of the second grating structure is arranged in the X direction with a second X repetition pitch $P_{R2X}$.

According to a further aspect, a plurality of portions of the second sub-area is arranged in the Y direction with a second Y repetition pitch $P_{R2Y}$.

According to a further aspect, the first X repetition pitch $P_{R1X}$ and the second X repetition pitch $P_{R1X}$ are equal.

According to a further aspect, the first Y repetition pitch $P_{R1Y}$ and the second Y repetition pitch $P_{R2Y}$ are equal.

According to a further aspect, the X and Y repetition pitches $P_{RX}$, $P_{RY}$ are equal.

It must be noted that the above mentioned aspects can be freely combined.

According to a further aspect, the portions of the first and second grating structures are equal in size. According to a further aspect, they can also have different sizes.

According to a further aspect of the invention, at least one portion of a third or more grating structures is provided with at least one further different grating orientation $G_{ON}$.

According to a further aspect of the invention, the first grating orientation $G_{O1}$ is arranged transverse to the second grating orientation $G_{O2}$.

In the examples shown, the first grating orientation $G_{O1}$ is arranged orthogonal to the second grating orientation $G_{O2}$, i.e. in 90° to the second grating orientation.

According to FIG. 7, an example is shown, where the portions of the first and second grating structures 26, 30 are arranged across the area of the analyzer grating 14 in a chessboard pattern 56. As schematically illustrated, a plurality of portions of the first grating structure 26 are arranged in the horizontal direction with a first repetition pitch $P_{R1X}$, indicated with reference numeral 58. Further, a plurality of the portions of the first grating structure 26 are arranged in the Y direction with the first repetition pitch $P_{R1Y}$, indicated with reference numeral 60. As can be seen, the first repetition pitches are equal in size.

Underneath the analyzer grating 14, the detector 12 is arranged. The sensor comprises sensor pixels 16 of the first sub-group 18 of pixels, which are covered by the portions of the first grating structure 26 of the analyzer grating 14. The sensor further comprises the sensor pixels 20 of the second sub-group of pixels 22, which are indicated with a dotted pattern, which pattern is only for explanation and is not referring to any structural difference of the sensor pixels of the first and second sub-groups.

FIG. 7a shows the first position P1, in which raw image data can be recorded by the sensor. As mentioned above, the sensor pixels 16 of the first sub-group of pixels record phase-gradient information according to the first grating orientation, whereas the sensor pixels 20 of the second sub-group of pixels 22 record phase-gradient information based on the second grating orientation.

By translating the grating, the portions 24 of the first sub-grating structure 26 are arranged in front of the sensor pixels 20 of the second sub-group of pixels 22. The pixels 16 of the first sub-group of pixels 18 is now arranged behind the portions 28 of the second grating structure 30. Thus, in the second position, as shown in FIG. 7b, the sensor pixels 16 of the sub-group of pixels 18 record phase-gradient information with relation to the second grating orientation, whereas the pixels 20 of the second sub-group of pixels 22 now record phase-gradient information relating to the first grating orientation.

The translation of the grating is indicated with a thick frame 62 in a dotted line indicating a particular portion with a grating structure of the first grating structure 26. However, the frame 62 is for illustrating purposes only.

In FIG. 7, the analyzer grating 14 has been translated with relation to the sensor in a horizontal way, wherein the sensor remains. Further, it must be noted that the illustrations show a section of a diffraction grating, i.e. a phase grating and analyzer grating, according to the invention. This can be seen in that, although moving the analyzer grating from FIG. 7a to FIG. 7b by one pitch to the right, the left column of FIG. 7b is also shown with respective grating fields.

Figure 8B:
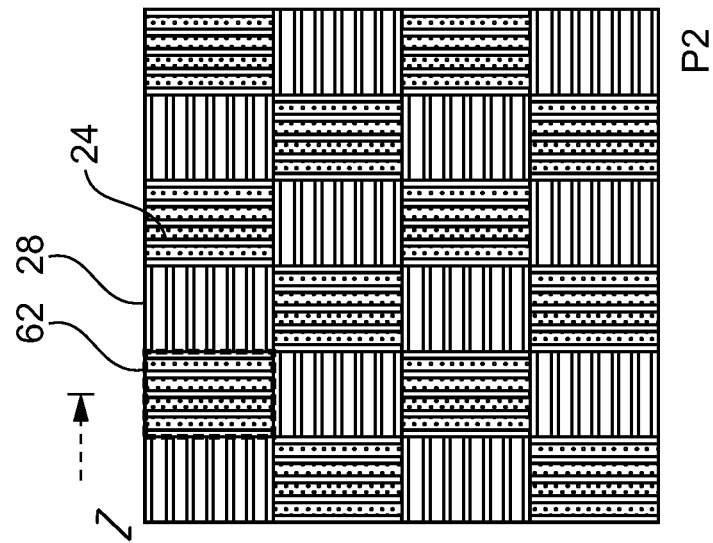
Figure 8A:
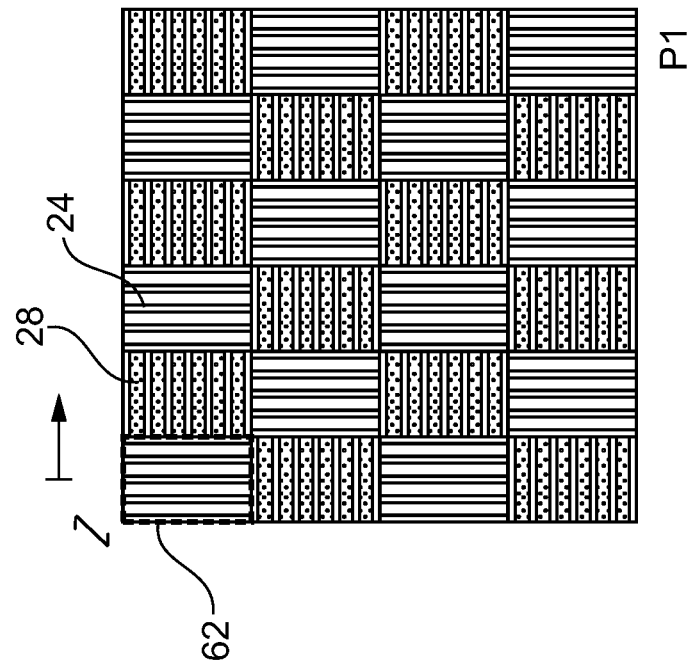

According to a further aspect of the invention (not shown), it is also possible to translate the analyzer grating in another direction, for example in the vertical direction. As shown in FIG. 8, the test board pattern can also be arranged with rectangular fields. As can be seen, the portions of the first and second grating structures are rectangular, wherein the extension in one direction differs from the extension in a second direction.

According to one aspect of the invention, as mentioned above, the grating pitch $P_{G1}$ of the first grating structure is equal to the grating pitch $P_{G2}$ of the second grating structure 30.

Of course, the analyzer grating 14 of FIG. 8 can also be moved in the vertical direction instead of the horizontal translation shown in FIG. 8.

According to a further aspect of the invention, shown in FIG. 9, portions of the first grating structure 26 are arranged linearly in at least one linear first grating group 76 comprising at least one line 78 of portions 24 of the first grating structure. Further, portions 28 of the second grating structure 30 are arranged linearly in at least one linear second grating group 80 comprising at least one line 82 of second grating structure. As can be seen in FIG. 9, at least two first grating groups 76 and at least two linear second grating groups 80 are provided. The grating groups are arranged in an alternating manner in a first line pitch $P_{L1}$ which is indicated with reference numeral 84. In order to provide phase-gradient information in both grating orientation directions for all sensor pixels, the analyzer grating is translated downwards in a vertical direction from FIG. 9a to FIG. 9b, which is once again illustrated by the frame 62.

In the above described Figures, i.e. FIGS. 4 to 9, the phase-stepping has been shown in an acute angle of 45° with respect to each of the grating orientations.

It must be noted that an acute angle leads to a stepping movement of both grating structures having different orientation. Thus, a projection leads to the effective stepping in an orthogonal way to the respective grating structures.

As mentioned above, it must be noted, that also other angles are possible. For example, if the two grating structures have orthogonally arranged grating orientations, i.e. they are arranged orthogonal to each other, smaller or larger angles with respect to the grating orientations are also possible.

For example, an angle clearly distinguishable from 45°, e.g. 30°, is applied for the phase-stepping direction. By stepping at a different angle than 45°; it is possible to distinguish between the phase gradient over the two parts of the pixel by the frequency of the modulation during phase-stepping. This allow for improved image information acquisition. For example, 30° to the first grating orientation, thus 60° to the second orientation, are also possible. Of course, also smaller/larger angles are possible, such as 10° and 80° to the first and second grating orientation, respectively. However, it must be noted that in case of smaller angles, the projection geometry of course leads to a decrease in the quality of the acquired image signals.

The aspect of a coherent radiation has already been mentioned with respect to FIGS. 2 and 3. By applying radiation which has coherence in two different directions, for example achieved by a grating arrangement according to FIG. 2 or 3, phase gradient information can be recorded in two different grating orientations, as for example shown in FIGS. 4 to 9.

According to a further exemplary embodiment (not shown), in case only radiation with coherence in one direction is available, the phase grating 15 and the analyzer grating 14 is rotated with an acute angle in order to achieve the possibility to acquire gradient information for two different directions, which is, once again, provided by a projection, since the so-to-speak linear coherent radiation is arranged in a rotated manner with respect to the grating structures of the first and second grating structures 26, 30.

A further aspect is explained in the following with reference to FIG. 10. In FIG. 10, a radiation 90 is applied which has a high transversal coherence in two directions, which is symbolically indicated by a grid with lines, for which the reference numeral 90 is used.

It is noted that the grid 90 is shown such that the corners of the square-like grid patterns extend beyond the grid, because the grid 90 only indicates the rotated orientation of coherence and grating structure and not the actual sizes. Of course, the gratings can be fully radiated with the radiation with two coherence directions, i.e. the detector and the gratings are radiated over their whole area.

According to another aspect, a radiation is provided that covers the gratings and/or the detector only partially.

The analyzer grating 14, and of course also the phase grating 15, are rotated with respect to the linear grating structure with an angle, for example 45°, which angle is indicated with reference numeral 92.

FIG. 10a shows a first position P1 in which first raw image data is acquired while phase-stepping the analyzer grating 14 in relation to one of the two coherencies of the radiation 90, e.g. the phase-stepping is performed in a horizontal manner, which is indicated by reference numeral 48'. Thus, a projection is achieved for both grating directions such that phase gradient information can be recorded for both grating directions.

Then, the analyzer grating 14 is translated to a second position P2, which is indicated with the same reference numerals as used in the Figures above. However, the translation occurs in relation to the pitch of the analyzer grating 14. In other words, the translation occurs in an upward direction to the right, namely 45° according to the acute angle 92. The translation can be seen by the dotted frame 62. Thus, with respect to a particular pixel, for example a pixel indicated with a dotted line frame 94, is provided with a portion 24 of the first grating structure 26 in the first position, and with a portion 28 of the second grating structure 30 in the second position.

It must be noted that the angle 92 of 45° is shown for illustration purposes only. Of course, different angles, for example in a range from 30° to 60° or even from 10° to 80° can be applied.

Due to the rotated arrangement, i.e. the acute angle 92, of the analyzer grating 14 with respect to the coherent radiation 90, the phase-stepping could also be achieved by stepping the analyzer grating 14 in a vertical manner as indicated with reference numeral 48", as shown in FIG. 11.

It must be noted that according to a further exemplary embodiment, the phase grating 15 is phase-stepped in the first and/or second position.

According to a further exemplary embodiment (not shown), coherent radiation with coherence in only one direction is provide, while phase-stepping the analyzer grating according to FIG. 10 or 11.

According to a further aspect of the invention, it is also possible to provide coherent radiation with coherence in two directions, while phase-stepping the analyzer grating in a first direction in a first phase-stepping and in a second direction in a second phase-stepping, wherein the stepping directions are perpendicular or orthogonal to each other. This is shown in FIG. 12.

Figure 12A:
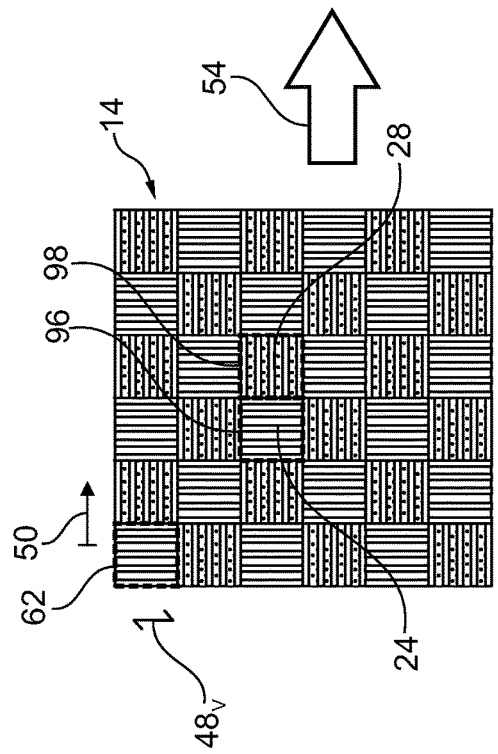

In a first step, shown in FIG. 12a, the analyzer grating is phase-stepped in a horizontal way, as indicated with reference numeral $48_H$. Thus, a particular pixel, for example a pixel indicated with a dotted frame 96, records phase gradient based information with respect to the first grating structure 26. The adjacent pixel, indicated with a second dotted frame 98, does not record phase gradient based information, since the phase-stepping occurs parallel to the grating structure of the portion 28 of the second grating structure 30.

Figure 12B:
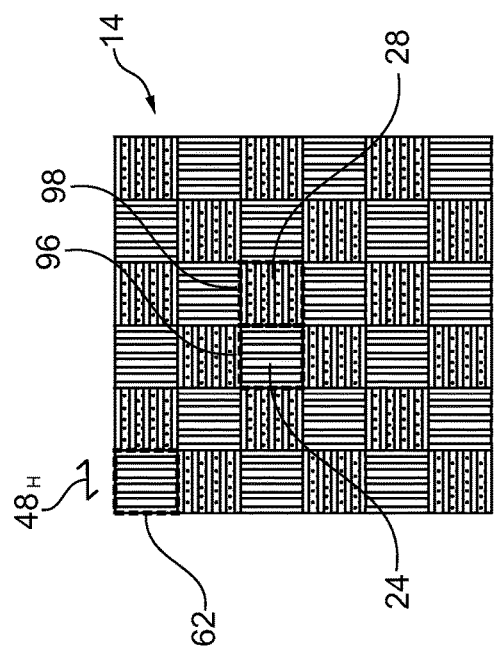

In a further phase-stepping step, shown in FIG. 12b, the analyzer grating 14 is phase-stepped in a vertical manner, indicated by reference numeral $48_V$. In this phase-stepping step, the pixel 96 does not record phase gradient based information since the stepping occurs parallel to the direction of the first grating structure 26 which covers this pixel. The adjacent pixel 98 now records phase gradient based information with respect to the second grating structure 30 which is arranged in front of this particular pixel.

Figure 12C:
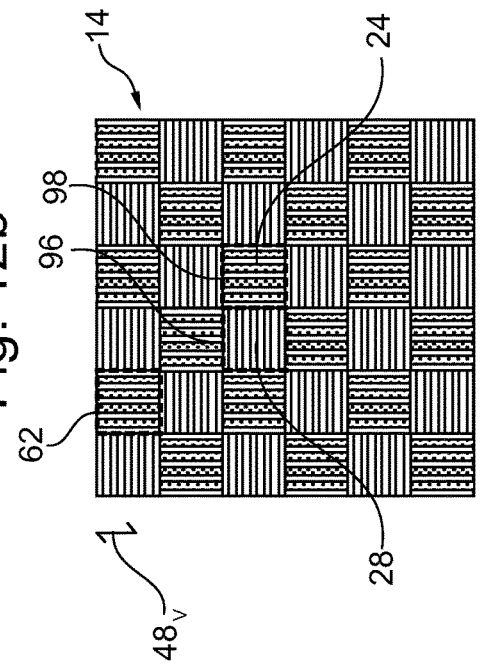
Figure 12D:
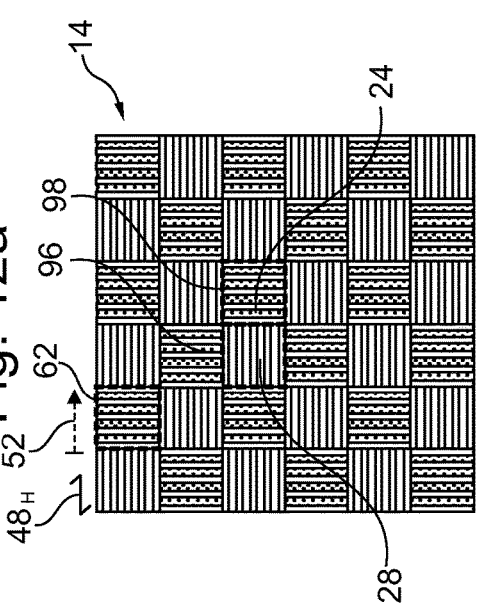

Next, a translation step is provided to translate the analyzer grating 14 from position P1, as shown in FIGS. 12a and 12b to position P2, which is shown in FIGS. 12c and 12d. In other words, FIG. 12c follows 12b.

In a third phase-stepping step, shown in FIG. 12c, the analyzer grating 14 is once again stepped in a horizontal manner, as indicated with double arrow $48_H$. In this position, the pixel 96 does not record phase gradient based information, since the phase-stepping direction is parallel to the grating structure of the second grating structure 30, now arranged in front of this particular pixel. The adjacent pixel 98 now records phase gradient based information with respect to the first grating structure, which is arranged in front of this particular pixel.

In a fourth phase-stepping step, shown in FIG. 12d, the analyzer grating 14 is stepped in a vertical manner, as indicated with reference numeral $48_V$. In this second position P2, by stepping vertically, the pixel 96 can now record phase gradient based information with respect to the second grating structure 30, which is arranged in front of this pixel. The adjacent pixel 98 does not record phase gradient based information, since the stepping occurs in a direction parallel to the grating structure of the first grating structure 26 arranged in front of this pixel in the second position.

According to a further exemplary embodiment, shown in FIG. 13, in the first and second position P1 and P2, the first and second grating structures 26, 30 of the analyzer grating 14 are each arranged at least partially in front of a first sub-group of pixels 18 and at least partially in front of the second sub-group of pixels 22. In the first and second position, different first and second parts of the first and second sub-group of pixels are covered by the portions of the first grating structure of the analyzer grating, respectively.

As schematically illustrated in FIG. 13, as an example, sensor pixels 16 of the first sub-group pixels 18 and sensor pixels 20 of the second sub-group of pixels 22 are shown; the sensor pixels 16, 20 are arranged in a chessboard pattern, which is indicated by a dotted pattern of the second pixels 20.

Further, an analyzer grating 14 is shown with portions 24 of the first grating structure 26 and portions 28 of the second grating structure 30. It is noted that the portions 28 of the second grating structure 30 are shown as being arranged perpendicular to the portions 24 of the first grating structure 26.

The analyzer grating 14 is provided with a chessboard pattern in which the portions 24 with the first grating structure 26 and the portions 28 with a second grating structure 30 are arranged in an alternating manner at both directions. Further, in FIG. 13a, the first position P1 is shown where the analyzer grating 14 is arranged displaced in relation to the sensor by half a pitch, wherein the pitch of the chessboard pattern of the sensor and the pitch of the chessboard pattern of the grating 14 are equal. Thus, each grating field, i.e. each portion 24 of the first grating structure 26 covers both half of the first pixel 16 and half of a sensor pixel 20. For example, a frame 192 indicates the first position of a particular grating field in FIG. 13a.

With reference to a particular sensor pixel, e.g. a pixel 94 in the third row of the sensor pixels being the third column of sensor pixels, the grating portion 24 covers a right half of the pixel 94 which is not further indicated. With reference to the adjacent pixel to the right, which is indicated with reference numeral 96, the grating field 24 covers its left half.

By translating the grating 14 with respect to sensor by one pitch, indicated by the translating arrow 54, the sensor pixel 94 is now partially covered by another grating field of the first grating structure 26. Thus, the grating structure now covers the left half of the sensor pixel 94.

With respect to the second grating structure 30, the other half of the pixel is covered with this grating structure.

Thus, one pixel receives radiation affected by the first grating structure as well as the second grating structure. In other words, one sensor pixel receives phase gradient information in relation to both grating structure directions.

Therefore, the phase-stepping is provided to be in an angle differing from 45°, as indicated with reference numeral 48.

For example, the phase-stepping is provided in an acute angle of 30° to the first grating structure and in an angle of 60° to the second grating structure. Thus, it is possible to distinct the information relating to the first grating structure from the phase gradient information relating to the second grating structure, since the two different angles result in two different signals overlapping on the sensor, but which single signals can be distinct from another due to their different period.

By translating the grating with respect to the sensor by one pitch, indicated by the translating arrow 54, a sensor pixel is now partially covered by the two grating structures, only in a different arrangement, i.e. the different half now records the respective gradient information.

In a third position P3, shown in FIG. 13c, the grating structure is arranged such that it covers the upper and lower halves of the sensor pixels with respect to the first grating structure instead of the right and left halves as shown in FIGS. 13a and 13b. The translation to the third position is indicated with a dotted line translating arrow 198.

From the third position, the grating is translated to a further position, in which further raw image data is recorded while applying coherent X-ray radiation and phase-stepping the analyzer grating. In the further position, the first and second sub-areas of the analyzer grating and the phase grating are each arranged at least partially in front of the first sub-group of pixels and at least partially in front of the second sub-group of pixels; wherein in the further position, different further parts of the first and second sub-group of pixels are covered by the portions of the first sub-area of the analyzer and phase grating respectively; which further parts partially overlap with the first and second parts respectively.

For example, as show in FIG. 13, by translating the grating from the third position P3 to the fourth position P4, which is shown in FIG. 13d, which translation is indicated by the translation arrow 54, the grating is moved downwards by one pitch, which his once again illustrated with the frame 192 throughout FIG. 13. In the fourth position P4, a particular pixel is now covered with the other grating structure in relation to FIG. 13c.

Thus, so far, four sets of raw image data are provided.

Further, a fifth position P5 is provided, into which the grating is translated and in which fifth raw image data is recorded while applying coherent X-ray radiation and phase-stepping the analyzer grating. In the fifth position P5, sub-parts of the first, second, third and fourth parts are covered by the portions of the first grating structure 26, and in a similar fashion with respect to the second grating structure 30.

Figure 13F:
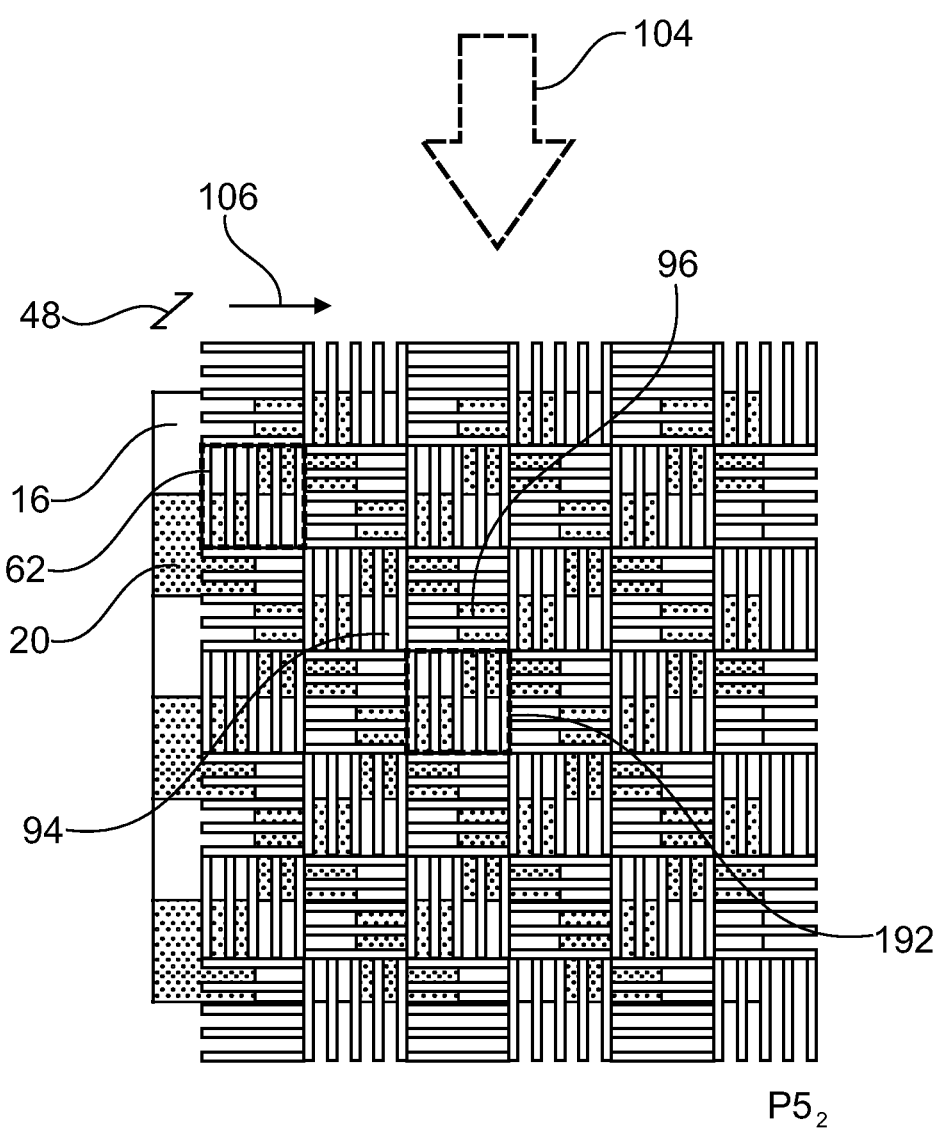

For the fifth position, two alterative possibilities are shown in FIG. 13e and FIG. 13f.

Starting with the fourth position, it is possible to achieve a first fifth position $P5_1$ as shown in FIG. 13e by translating the analyzer grating by half a pitch, which is indicated with dotted line translation arrow 100 and a pitch indicator arrow 102, which has half the dimension of the previous pitch arrow. As can be seen by the frame 192, each grating field of the analyzer grating 14 of the first grating structure 26 now covers four sensor pixels at one time, namely two first sensor pixels and two second sensor pixels.

An alternative fifth position $P5_2$ is shown in FIG. 13f, which can be achieved starting from the third position by translating the analyzer grating 14 by half a pitch to the right, which is indicated with a dotted line translating arrow 104 and half a pitch arrow 106.

As can be seen, in the fifth position $P5_2$, sub-parts of the first, second, third and fourth parts are covered by the portions of the grating fields relating to the first grating structure 26 of the analyzer grating 14. Thus, parts of the sensor pixels are covered in a so-to-speak mirrored manner with reference to FIG. 13e.

With reference to FIG. 13, it is possible to achieve a spatial resolution improvement by a factor of 2, while receiving phase gradient information for both grating directions in either the horizontal direction, which is shown in FIGS. 13a and 13b, or in the vertical direction, which is shown in FIGS. 13c and 13d.

As explained above, for each of the translational positions of the analyzer grating, an entire phase-stepping loop has to be performed. By only performing the steps of FIGS. 13a and 13b or the steps of FIGS. 13c and 13d, the resolution can be improved either in the vertical or in the horizontal direction, but not in both directions at the same time.

An embodiment for which this is possible, as explained above, is illustrated by FIG. 13e or 13f. In other words, if the four phase-stepping procedures of FIGS. 13a to 13d are supported by either of the two stepping cycles shown in FIG. 13e or 13f, the spatial resolution can be improved in a vertical and a horizontal direction simultaneously. Thus, from the five resulting phases, the phase gradient in each quarter of the indicated pixel in FIGS. 13a to 13d, in combination with either FIG. 13e or FIG. 13f can be computed for both grating orientations.

According to a further exemplary embodiment, the phase grating 15 is phase-stepped in at least one of the group of first, second, third, fourth and fifth position.

According to a further exemplary embodiment, the fourth acquisition step is not applied, but the fifth acquisition step is provided instead. Thus, it is also possible to achieve enhanced image data for further processing due to the following computational steps. For example, in position P1, for pixel 96, a+c=m1 is measured; in position P2, b+d=m2 is measured and in position P3 a+b=m3.

In position P4, c+d=m4 would be measured. The matrix thus obtained for this system of linear equations would be singular. As mentioned above, if measurement P4 is omitted and position P5 is measured instead, leading to the sequence P1,P2,P3,P5:

$$A \cdot x = m \text{ with}$$

$$\begin{pmatrix} 1 & 0 & 1 & 0 \\ 0 & 1 & 0 & 1 \\ 1 & 1 & 0 & 0 \\ 1 & 0 & 0 & 1 \end{pmatrix} \begin{pmatrix} x_a \\ x_b \\ x_c \\ x_d \end{pmatrix} = \begin{pmatrix} m_1 \\ m_2 \\ m_3 \\ m_4 \end{pmatrix}$$

According to a further exemplary embodiment, instead of the fourth and fifth position, one of the fifth positions ($P5_1$; $P5_2$) is provided into which the analyzer grating and the phase grating are translated (464) and in which fifth raw image data is recorded (474) while applying (470) coherent X-ray radiation and phase-stepping (472) the analyzer grating; wherein in the fifth position, sub-parts ($94e_1, 94e_2, 96e_1, 96e_2; 94f_1, 94f_2, 95f_1, 95f_2$) of the first, second, third and fourth parts are covered by the portions of the first sub-areas of the analyzer grating and the phase grating.

According to a further exemplary embodiment, not further shown, the X-ray radiation is applied to the phase and analyzer grating which is coherent only in one direction. Further, the analyzer grating 14 and the phase grating 15 are rotated by an acute angle, for example by 45°, and the phase-stepping occurs either parallel or orthogonal to the coherence of the X-ray radiation.

According to a further aspect of the invention, at least one portion 202 of a second sub-area 204 is provided, wherein the second sub-area is X-ray transparent and wherein the at least one portion of the second sub-area provides and X-ray transparent aperture 206 in the grating. Further, portions of the first sub-area 23 and the second sub-area 204 are arranged in an alternating manner in at least one direction.

For example, a number of portions of the first and/or second sub-areas are arranged adjacent as first subsets and/or second subsets. For example, the first and/or second subsets are arranged across the area of the diffraction grating in a first subset repetition pitch $P_{SR1}$ and/or second subset repetition pitch $P_{SR2}$ in at least one direction (not further shown).

Figure 14:
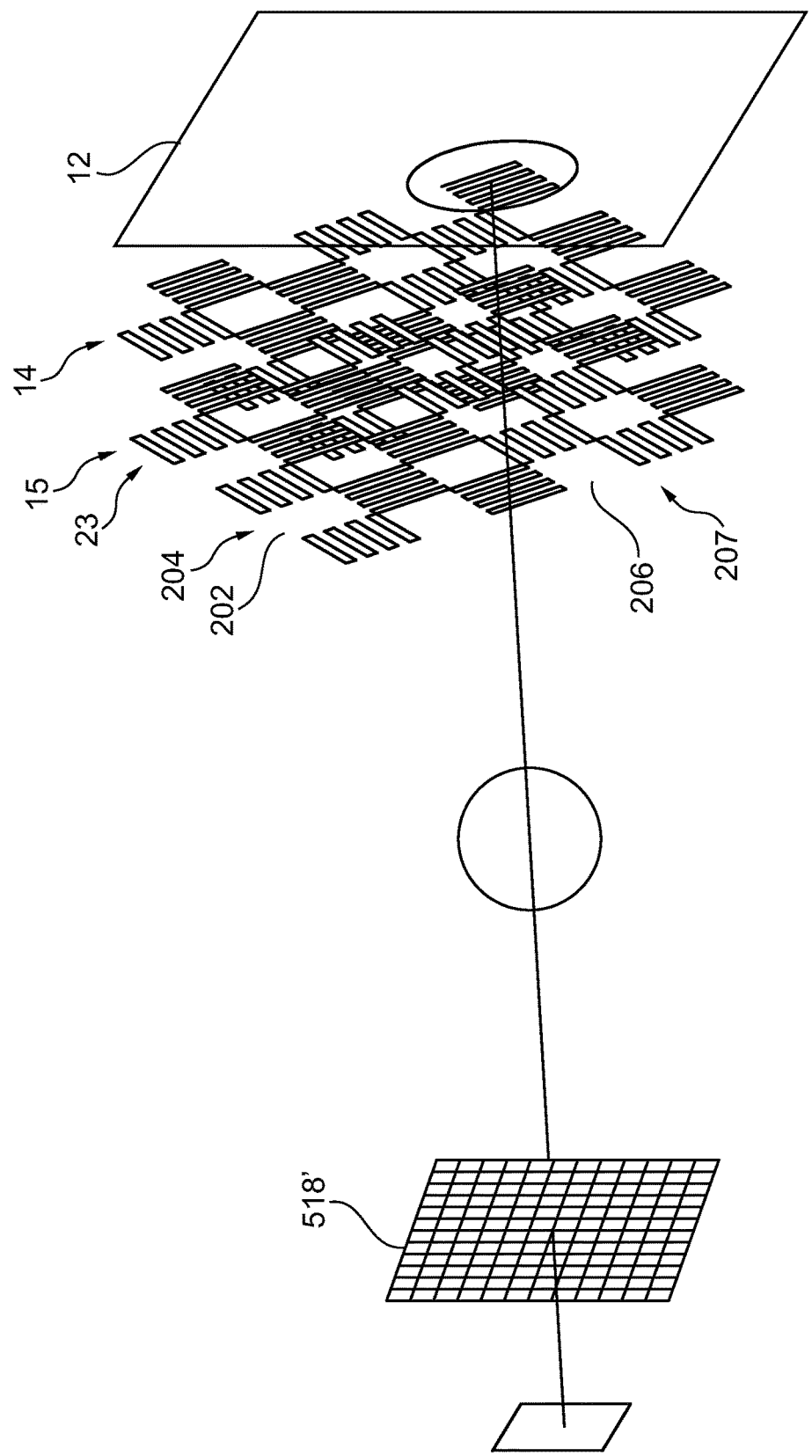
FIG. 14 schematically shows a further exemplary embodiment of an X-ray image acquisition device for generating phase contrast images according to the invention.

According to a further exemplary embodiment of the invention, the portions of the first and second sub-areas 23, 204 are arranged across the area of the diffraction grating in a chessboard configuration 207, as shown in FIG. 14.

For example, the portions of the first and second grating structures 26, 30 are arranged in an alternating manner per row and column, i.e. every second field is having a grating structure, but wherein the grating structure varies. In other words, a portion of the first grating structure 26 is provided in every fourth field.

According to a further example, the portions of the first and second grating structures 26, 30 are arranged in an alternating manner in the diagonal direction.

According to a further example, a pattern is provided in which several portions are combined to sub-fields with first or second grating structures, which sub-fields are provided in an alternating manner in one or two directions.

According to a further aspect, the sub-fields can have different sizes, i.e. different numbers of portions are combined.

As can be seen in FIG. 14, the analyzer grating 14 and the phase grating 15 are both provided with a chessboard pattern, in which every second field is provided as a portion of the second sub-area 204. The gratings are rotated by 45° with respect to one of the two directions of the source grating 518' which is providing radiation with transversal coherence in two directions.

In FIG. 15, the respective steps are shown. First, as indicated in FIG. 15a, coherent radiation 90 with coherence in two directions is applied to the grating structures 14, 15, which grating structures are arranged in an acute angle, for example an angle of 45° as indicated with reference numeral 92.

Of course, other acute angles are also possible, for example between 10° and 80° or in particular between 30° and 60°.

With relation to a particular pixel, indicated with dotted frame 292, in a first phase-stepping step, gradient information is achieved with respect to the first grating orientation. The phase-stepping is performed in a horizontal manner $48_H$, i.e. perpendicular to one of the directions of the coherent radiation structure, which coherence is indicated with the reference numeral 90. Next, the gratings 14 and 15 are translated from position P1 in FIG. 15a to position P2 in FIG. 15b, wherein the translation is provided with relation to the grating, i.e. in an angle of 45° with respect to the coherence of the radiation 90, i.e. parallel to one of the axis of the chess-board grating structure. Thus, the pixel 292 can now record density information in position P2, since the portion 202 of the second sub-area 204 is provided as an X-ray transparent aperture in the grating. Of course, the grating parts contain some intensity information, too. For example, the grating portions provide some information about the mean attenuation, e.g. by averaging over the phase-stepping scans. However, the distinction above refers more to the general difference for illustration.

Figure 15D:
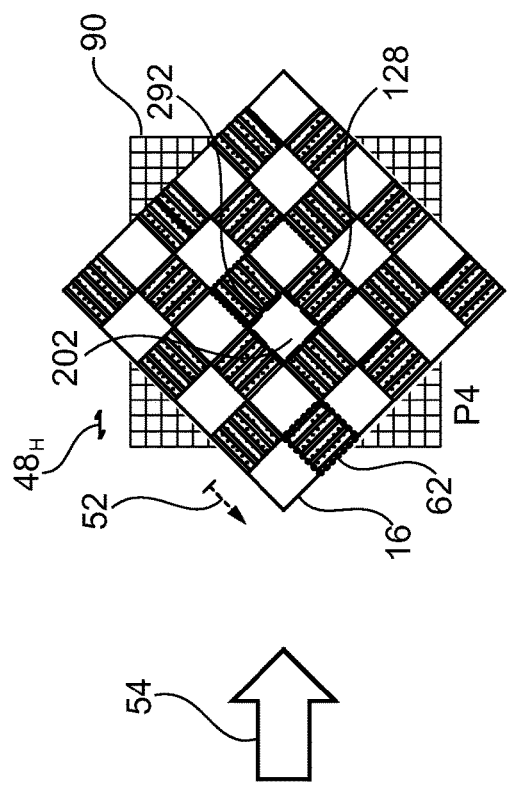
Figure 16D:
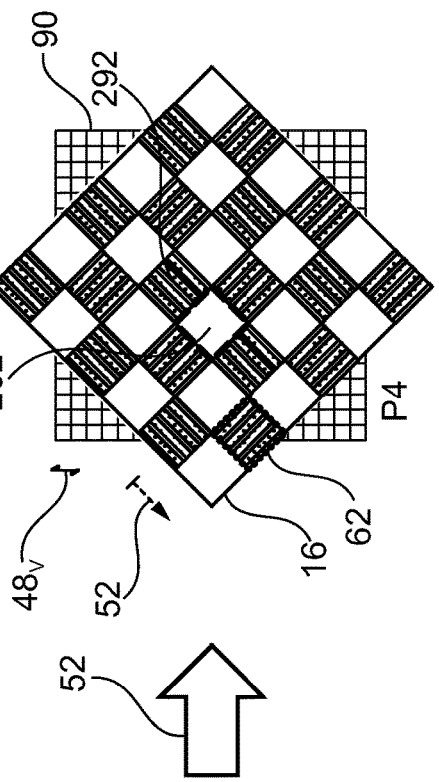
Figure 15C:
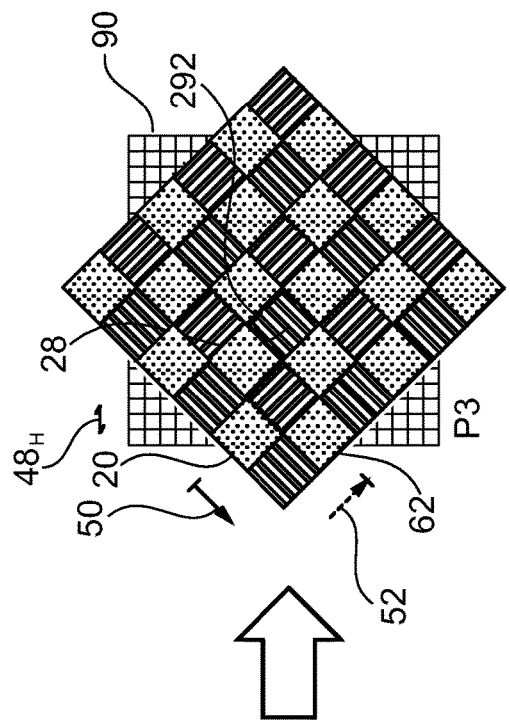
Figure 16C:
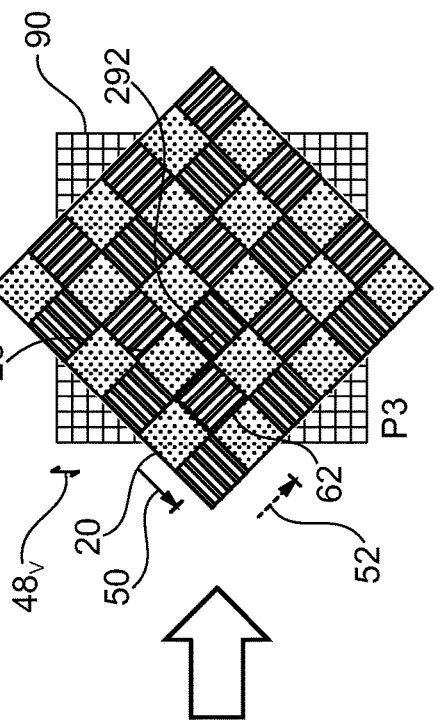

By a further translation step, the gratings are translated to a third position P3, shown in FIG. 15c. In this position, a further phase-stepping is performed, thus, pixel 292 now records phase gradient information with respect to the second grating orientation now covering the particular sensor pixel.

By a further translation step, the gratings are translated from the third position P3 to a fourth position P4, shown in FIG. 15d. In this position, the pixel 292 again records density information since in this position a portion 202 of the second sub-area 204 is arranged in front of this particular pixel.

Of course, in the second position P2 and the fourth position P4, phase-stepping is also applied since phase gradient information is recorded for every second other pixel of the sensor in these two positions, too.

Of course, the phase-stepping can be performed in a vertical manner, which is indicated with respective FIGS. 16a to 16d.

According to another aspect, the phase-stepping can be performed in a horizontal manner in one position and in a vertical manner in another position (not shown).

According to a further exemplary embodiment, although not further shown, instead of rotating the grating structure with respect to the linear coherent radiation, the radiation with coherence in two directions is provided and the phase-stepping is provided in an acute angle with respect to the grating structure, i.e. a diagonal stepping is performed in a similar way as described with relation to FIG. 7, for example.

According to an aspect of the invention, the phase-stepping is performed in a 45° angle with respect to the grating structure.

According to a further aspect, the angle of the phase-stepping is 30°, for example.

By providing a grating structure with two sub-areas, one of which sub-areas is comprising a grating structure with two different grating directions, and the other one of which sub-areas is provided as X-ray transparent apertures, it is possible to acquire phase gradient information image data as well as density information image data, i.e. so-to-speak conventional X-ray images in combination with phase gradient information. It must be noted that the same X-ray dose is applied to a patient, for example, compared with the necessary steps to acquire the same type of information. However, one of the advantages is that a replacement or removal of any of the gratings is not necessary during the information. In other words, the two image types can be acquired at the same time and can thus be provided to the user simultaneously, for example by presenting them next to each other or also by combining them to an enhanced X-ray image.

According to a further exemplary embodiment (not shown), instead of the transversal coherence in two directions of FIG. 14, coherence in only one direction is provided, e.g. with a linear source grating.

Figure 17:
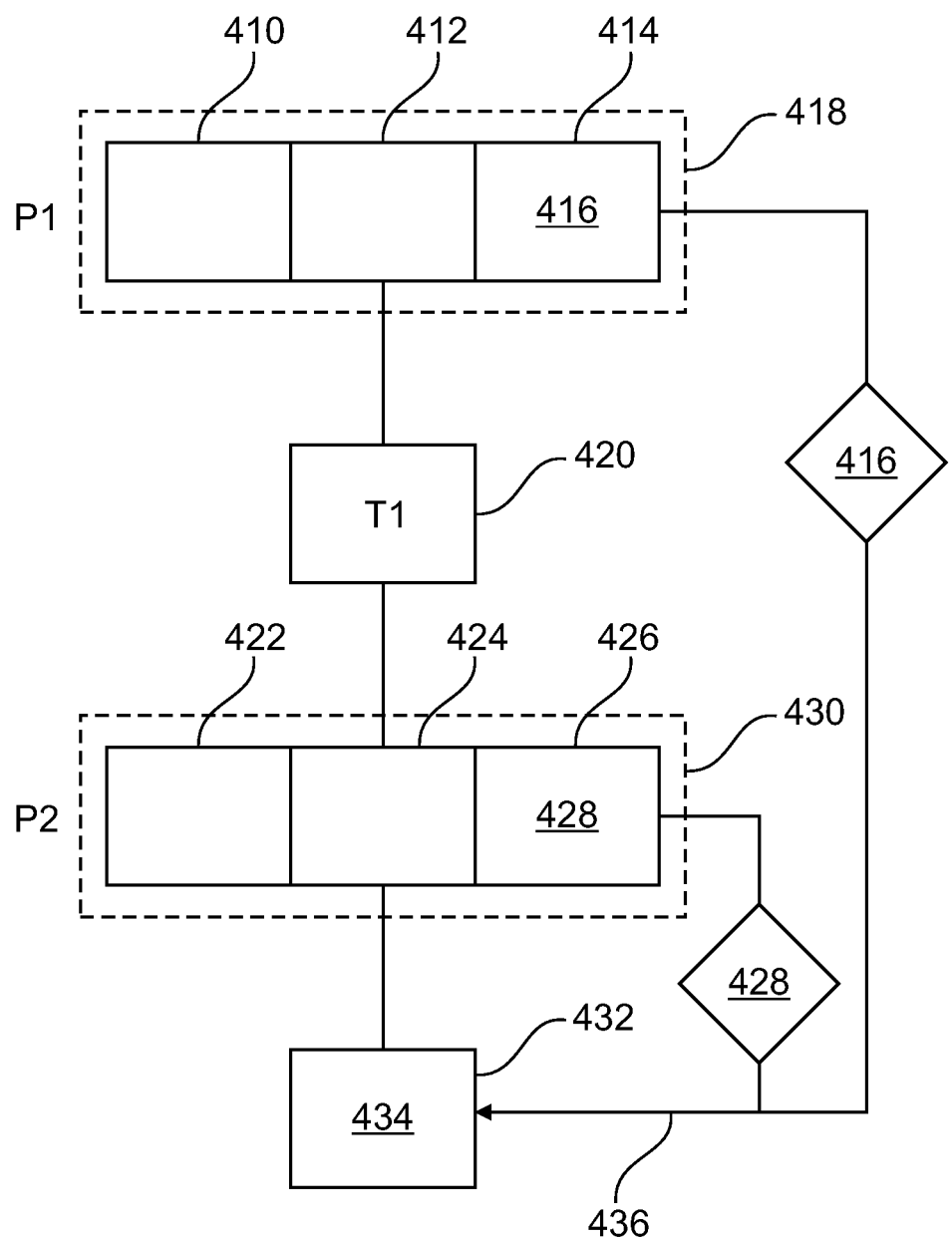
FIG. 17 shows basic method steps of an exemplary embodiment of the invention.

According to a further exemplary embodiment, a method 400 for differential phase contrast imaging is provided, which is explained with reference to FIG. 17.

The method comprises the following steps: In a first position P1, in a first application step 410, coherent X-ray radiation is applied to a phase grating and an analyzer grating in the first position P1. The phase grating and the analyzer grating each comprise at least two parts with different grating orientations, wherein the first diffraction grating is a phase grating and wherein the second diffraction grating is an analyzer grating. Next, in a phase-stepping step 412, the analyzer grating is phase-stepped, and in a recording step 414, first raw image data 416 is recorded with a sensor with at least two parts, wherein the first and the second part are recording phase contrast information relating to the first and second grating orientations. The three steps 410, 412, and 414 are performed at the same time which is indicated with a dotted line rectangular 418 surrounding the three steps.

Further, in a translation step T1, indicated with reference numeral 420, the phase grating and the analyzer grating are translated to a second position P2.

Then, in a second application step 425, coherent X-ray radiation is applied to the phase grating and the analyzer grating in the second position. During the application, in a second phase-stepping step 424, the analyzer grating is phase-stepped. At the same time, in a second recording step 426, second raw image data 428 is recorded with a sensor with at least two parts, wherein the first and second part are recording phase contrast information relating to the second and the first grating orientations. The simultaneous performing of the three steps 422, 424, and 426 is indicated with a second dotted line rectangular 430.

Further, in a provision step 432, the recorded first and second raw image data is provided as raw image data 434. The combination of the first and second raw image data 416, 428 is indicated with an arrow 436.

The application step 410 is also referred to as step aa1), the phase-stepping step 412 as step aa2), the recording step 414 as step aa3), the translating step 420 as step b), the second application step 422 as step cc1), the second phase-stepping step 424 as step cc2), the second recording step 426 as step cc3), and the provision step 432 as step d).

According to a further exemplary embodiment, not shown, the diffraction gratings each comprise at least one portion of a first grating structure and at least one portion of a second grating structure, wherein the first grating structure comprises a plurality of bars and gaps with a grating orientation, being arranged periodically. The bars are arranged such that they change the phase and/or amplitude of an X-ray radiation and the gaps are X-ray transparent. The second grating structure comprises a plurality of bars and gaps with a second grating orientation, being arranged periodically. The bars are arranged such that they change the phase and/or amplitude of an X-ray radiation and the gaps are X-ray transparent. The first grating orientation is different than the second grating orientation.

According to a further aspect, the first and second raw image data are provided as two different images.

According to a further aspect, the raw image data is provided as one single image representing gradient information relating to both grating orientations.

According to one aspect, the coherent radiation is coherent in one direction, and this coherence direction is arranged in an acute angle in relation to the first and/or second grating orientation, for example 45° or in a range of 30° to 60°.

According to a further aspect, the analyzer grating is phase-stepped in an acute angle, for example of 45° or 30°, to the second or first grating structure in the phase-stepping steps mentioned above.

According to a further aspect, the phase-stepping direction in step aa2) is parallel to the phase-stepping direction in step cc2).

According to a further exemplary embodiment, not further shown, in step aa2), the phase grating is stepped transverse the first grating orientation. In step cc2), the phase grating is stepped transverse the second grating orientation. In step aa3), as primary first raw image data, phase contrast image information is recorded relating to the first grating orientation with the first parts of the sensor. In step cc3), as primary second raw image data, phase contrast information is recorded relating to the second grating orientation with the first parts of the sensor. In the first position P1, following steps aa1) to aa3), the following steps are performed before step b): ab1) applying coherent X-ray radiation to the interferometer, while ab2) phase-stepping the analyzer grating transverse the second grating orientation and ab3) recording secondary first raw image data with the sensor, wherein the second parts of the sensor are recording phase contrast information relating to the second grating orientation. In the second position P2, following steps cc1) to cc3), the following steps are performed: cd1) applying coherent X-ray radiation to the interferometer, while cd2) phase-stepping the analyzer grating transverse the first grating orientation, and cd3) recording secondary second raw image data with the sensor, wherein the second parts of the sensor are recording phase contrast image information relating to the first grating orientation.

The above mentioned example is also illustrated in FIGS. 12a to 12d.

According to a further aspect, the coherent radiation is coherent in one direction, and this coherence direction is arranged in an acute angle in relation to the first and/or second grating orientation. For example, the angle is 45°.

According to another aspect, the coherent radiation is coherent in two directions, one of which is parallel to the first grating orientation and the other one is parallel to the second grating orientation.

Figure 18:
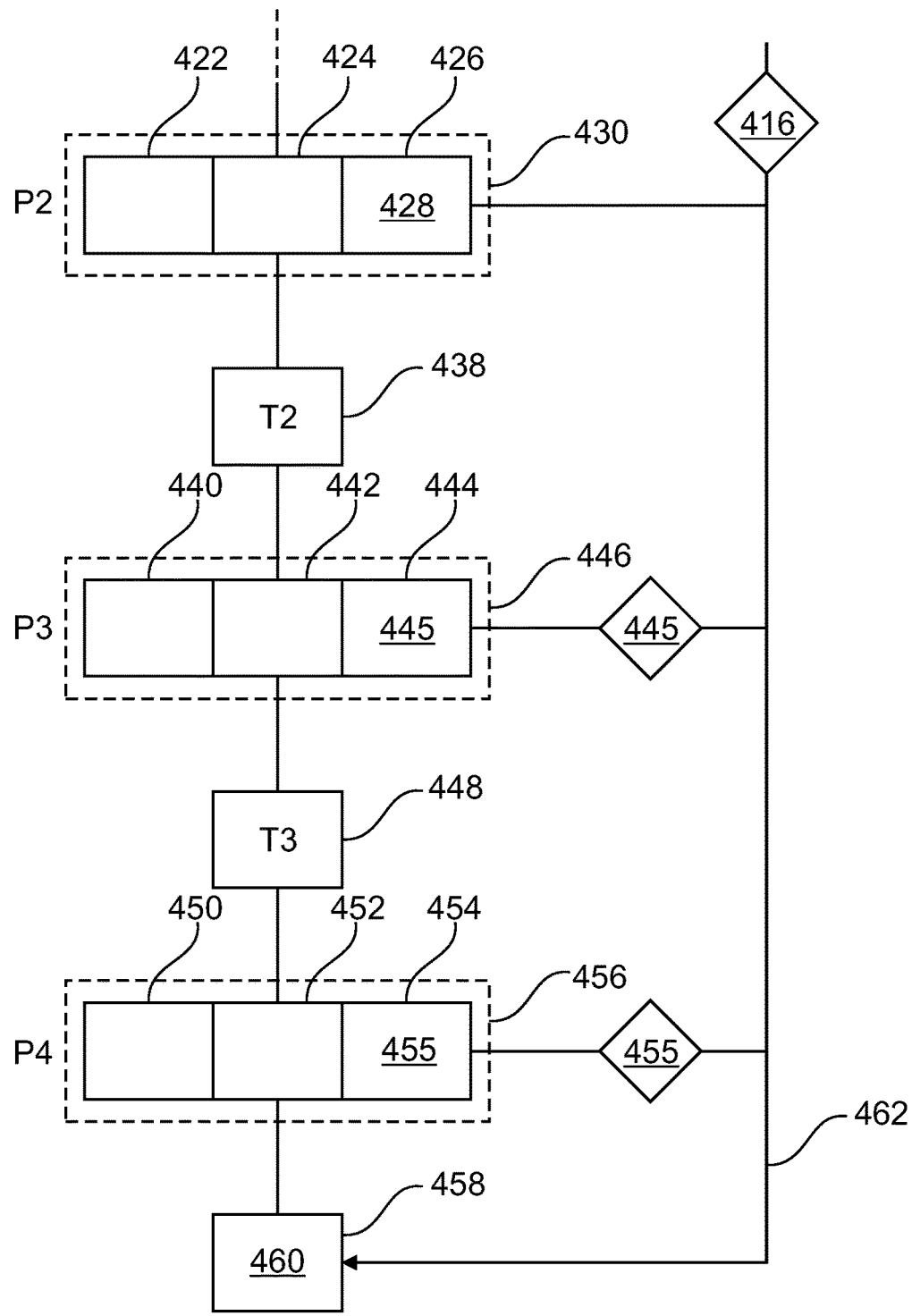
FIG. 18 shows a further exemplary embodiment of a method according to the invention.

According to a further exemplary embodiment, shown in FIG. 18, a method is provided, in which, following the second acquisition step indicated with a second dotted line rectangular 430, a second translation step T2, indicated with reference numeral 438, is provided in which the phase grating and the analyzer grating are translated to a third position P3. In the third position, a third application step 440, a third phase-stepping step 442, and a third recording step 444 are provided in a similar fashion as the respective steps described above with reference to FIG. 17. Once again, these steps, providing third image data 445, are performed simultaneously which is indicated with a third dotted line rectangular 446.

Further a third translation step T3, indicated with reference numeral 448, is provided in which the phase grating and the analyzer grating are translated to a fourth position P4. In this fourth position, a fourth application step 450, a fourth phase-stepping step 452, and a fourth recording step 454, providing fourth image data 455 are provided simultaneously, which is indicated by a fourth rectangular in dotted line, with reference numeral 456.

Thus, first, second, third, and fourth raw image data are provided, which, in a providing step 458, are provided as raw image data 416, wherein the combination and computational steps are indicated with arrow 462.

Figure 19:
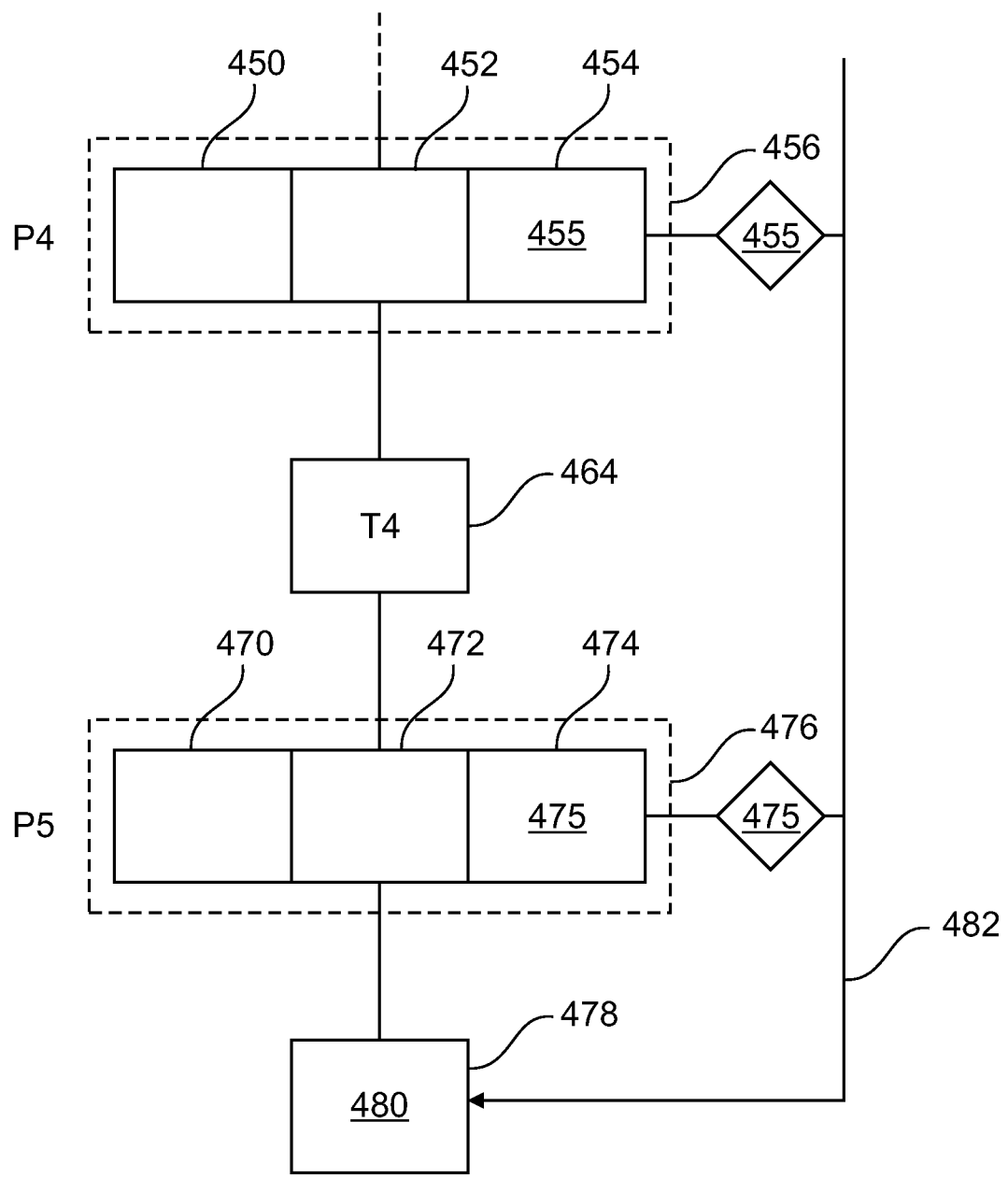
FIG. 19 shows a further exemplary embodiment of a method according to the invention.

According to a further exemplary embodiment, shown in FIG. 19, following the fourth acquisition in position P4, a fourth translation step T4, indicated with reference numeral 464, is performed in which the grating is translated into a fifth position P5, in which fifth raw image data 475 is recorded 474, while applying 470 coherent X-ray radiation and phase-stepping 472 the analyzer grating. In the fifth position, sub-parts of the first, second, third, and fourth parts are covered by the portions of the first grating structures and the second grating structures, respectively. The X-ray applying, recording, and phase-stepping steps are provided at the same time, which is indicated with a dotted line rectangular 476. Then, the recorded first, second, third, fourth, and fifth raw image data sets are provided 478 as raw image data 480. Of course, computational steps are provided in order to provide the raw image data 480. The combination and computational steps are indicated with arrow 482.

According to a further exemplary embodiment of one of the methods described above, the phase grating is phase-stepped in at least one of the group of first, second, third, fourth and fifth position.

In another exemplary embodiment of the present invention, a computer program or a computer program element is provided which is characterized by being adapted to execute the method steps of a method according to one of the preceding embodiments, on an appropriate system. The computer program may be stored and/or distributed on a suitable medium, such as an optical storage medium or a solid state medium supplied together with or as part of other hardware, but may also be distributed in other forms, such as via the internet or other wired or wireless telecommunication systems.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

Any reference signs in the claims should not be construed as limiting the scope.

The invention claimed is:

1. A diffraction grating configured for X-ray differential phase-contrast imaging, comprising:
multiple bars and multiple interleaving gaps,
wherein at least a first grating comprises both a plurality of said multiple bars with a first grating orientation $G_{O1}$ and, interleaving with the plurality of said multiple bars, a plurality of corresponding ones of said multiple interleaving gaps with said first grating orientation $G_{O1}$, said plurality of said multiple bars and said plurality of corresponding ones of said multiple interleaving gaps being arranged periodically; wherein said plurality of said multiple bars are arranged such that said plurality of said multiple bars change, for X-ray radiation being applied for X-ray differential phase-contrast imaging to said diffraction grating configured for X-ray differential phase-contrast imaging, at least one of phase and amplitude, said plurality of corresponding ones of said multiple interleaving gaps being X-ray transparent;
wherein at least a second grating, arranged side-by-side with said first grating so that the first grating and the second grating are both disposed to directly receive X-ray radiation, comprises a plurality from among a remainder of said multiple bars with a second grating orientation $G_{O2}$ and, interleaving with said plurality from among a remainder of said multiple bars of said second grating, a plurality of respective ones of said multiple interleaving gaps with said second grating orientation $G_{O2}$, said plurality from among a remainder of said multiple bars of said second grating and the plurality of respective ones of said multiple interleaving gaps of said second grating being arranged periodically; wherein said plurality from among a remainder of said multiple bars of said second grating are arranged such that said plurality from among a remainder of said multiple bars of said second grating change, for X-ray radiation being applied for X-ray differential phase-contrast imaging to said diffraction grating configured for X-ray differential phase-contrast imaging, at least one of phase and amplitude, said plurality of respective ones of said multiple interleaving gaps of said second grating being X-ray transparent; and
wherein said first grating orientation $G_{O1}$ is different than said second grating orientation $G_{O2}$.

2. The diffraction grating according to claim 1, wherein said first grating orientation $G_{O1}$ is arranged transverse to said second grating orientation $G_{O2}$.

3. The diffraction grating according to claim 1, wherein the at least a first grating comprises multiple first gratings and the at least a second grating comprises multiple second gratings,
from among said multiple bars and said multiple interleaving gaps, the multiple first gratings having both bars and interleaving gaps with said first grating orientation $G_{O1}$, and, from among said multiple bars and said multiple interleaving gaps, the multiple second gratings having both bars and interleaving gaps with said second grating orientation $G_{O2}$,
said multiple first gratings and said multiple second gratings collectively being arranged side-by-side so as to be disposed to directly receive X-ray radiation.

4. The diffraction grating of claim 3, ones from among said multiple first gratings and from among said multiple second gratings being arranged across said diffraction grating in a chess-board pattern, alternation in said chess-board pattern being based on whether a grating is from among said multiple first gratings or instead from among said multiple second gratings.

5. The diffraction grating of claim 3, wherein said plurality from among a remainder of said multiple bars of said second grating are straight and mutually parallel.

6. The diffraction grating according to claim 1, wherein the at least a first grating comprises multiple first gratings and the at least a second grating comprises multiple second gratings, from among said multiple bars and said multiple interleaving gaps, the multiple first gratings having both bars and interleaving gaps with said first grating orientation $G_{O1}$, and from among said multiple bars and said multiple interleaving gaps, the multiple second gratings having both bars and interleaving gaps with said second grating orientation $G_{O2}$, said diffraction grating comprising a first sub-area that includes said multiple first gratings and said multiple second gratings, said diffraction grating further comprising a second sub-area that includes at least one X-ray transparent portion that provides an X-ray transparent aperture in said diffraction grating; and wherein ones of said multiple first gratings and said multiple second gratings in said first sub-area and one or more of said at least one X-ray transparent portion in said second sub-area are arranged in an alternating manner in at least one direction, the alternation being based on belonging to either said first sub-area or said second sub-area.

7. The diffraction grating according to claim 6, said at least one X-ray transparent portion comprises multiple X-ray transparent portions, said diffraction grating having an area comprising said first sub-area and said second sub-area, ones from among said multiple first gratings and said multiple second gratings of said first sub-area and ones from among said multiple X-ray transparent portions of said second sub-area being arranged across said area of the diffraction grating in a chess-board configuration, alternation in said chess-board pattern being based on belonging to either said first sub-area or said second sub-area.

8. The diffraction grating of claim 1, wherein said plurality of corresponding ones of said multiple interleaving gaps are individually characterized as having a particular orientation in a plane, said particular orientation being said first grating orientation $G_{O1}$.

9. The diffraction grating of claim 1, wherein the plurality of corresponding ones of said multiple interleaving gaps individually are elongated.

10. A detector arrangement of an X-ray system for generating phase-contrast images of an object, said detector arrangement comprising:
a first diffraction grating;
a second diffraction grating;
a detector with a sensor; and
a processing unit;
wherein said sensor comprises at least one sensor pixel of a first sub-group of pixels and at least one sensor pixel of a second sub-group of pixels;

wherein said first diffraction grating is a phase grating;
wherein said second diffraction grating is an analyzer grating;
wherein said phase grating and said analyzer grating serve as diffraction gratings for X-ray differential phase-contrast imaging according to claim 1; wherein said analyzer grating is disposed at an orientation and has a first pitch $P_{G1}$ and a second pitch $P_{G2}$; wherein said processing unit is configured for stepping at least one of said analyzer grating and said phase grating in a predetermined relation to at least one of said orientation of said analyzer grating, said first pitch $P_{G1}$, and a second pitch $P_{G2}$; wherein said processing unit is further configured for translating in relation to said sensor each of the phase grating and the analyzer grating from a first position (P1) to at least a second position (P2) with a first translation pitch $P_{T1}$; wherein said first translation pitch $P_{T1}$ is adapted to a size of a grating structure from among those of the at least a first grating and the at least a second grating of said phase grating and of said analyzer grating; and wherein in the first position and the second position, different fractions of said sensor are arranged behind collectively the at least a first grating and the at least a second grating, this being so for each of said phase grating and said analyzer grating.

11. The detector arrangement according to claim 10, wherein said analyzer grating is adapted to be phase-stepped at an acute angle to at least one from among collectively the at least a first grating and the at least a second grating of said phase grating and of said analyzer grating.

12. An X-ray image acquisition device for generating phase-contrast images of an object, comprising:
an X-ray source;
a source grating; and
the detector arrangement of claim 10;
wherein said X-ray source generates an X-ray beam of polychromatic spectrum of X-rays; wherein said source grating is adapted to split said X-ray beam of polychromatic spectrum of X-rays into a splitted beam; and wherein said phase grating is adapted to recombine said splitted beam in an analyzer plane.

13. A medical X-ray imaging system for differential phase contrast imaging, comprising:
an X-ray image acquisition device for generating phase-contrast images of an object according to claim 12;
an interface unit; and
an object-receiving device;
wherein said processing unit is adapted to control said X-ray source as well as the phase-stepping of said analyzer grating and the translation of said phase grating and said analyzer grating;
wherein said interface unit is adapted to provide first raw image data and second raw image data, both recorded by said detector, to said processing unit; and
wherein said object-receiving device is adapted to receive an object of interest for phase contrast image acquisition.

14. A non-transitory computer readable medium embodying a program for differential phase contrast imaging, said program having instructions executable by a processor for performing a plurality of acts, from among said plurality there being the acts of:
aa1) applying coherent X-ray radiation to an interferometer that comprises a first diffraction grating and a second diffraction grating that are both in a first position (P1); each of said first diffraction grating and said second diffraction grating including at least two parts with respective grating orientations that differ from each other; wherein said first diffraction grating is a phase grating, a first part from among said at least two parts of said phase grating having a first grating orientation, and wherein said second diffraction grating is an analyzer grating, a second part from among said at least two parts of said analyzer grating having a second grating orientation;
aa2) phase-stepping said analyzer grating; and
aa3) recording, in conjunction with the act aa2), first raw image data with a sensor that includes at least two parts; wherein a first part, from among said at least two parts of said sensor, and a second part, from among said at least two parts of said sensor, are recording phase contrast image information relating correspondingly to the first grating orientation and the second grating orientation;
b) translating the analyzer grating and the phase grating to a second position (P2);
cc1) applying coherent X-ray radiation to the interferometer in the second position;
cc2) phase-stepping said analyzer grating;
cc3) recording, in conjunction with the act cc2), second raw image data with said sensor, wherein said first part and said second part are recording phase contrast image information relating correspondingly to the second grating orientation and the first grating orientation; and
d) providing the recorded first raw image data and second raw image data as raw image data.

15. The non-transitory computer readable medium of claim 14, wherein each of said first diffraction grating and said second diffraction grating includes a first grating structure and a second grating structure; wherein said first grating structure comprises a plurality of bars with a first grating orientation $G_{O1}$ and a plurality of gaps with said first grating orientation $G_{O1}$, said plurality of bars and said plurality of gaps being arranged periodically; wherein said plurality of gaps are X-ray transparent; wherein said plurality of bars are arranged so as to change at least one of phase and amplitude of an X-ray radiation; wherein said second grating structure comprises a plurality of bars with a second grating orientation $G_{O2}$ and a plurality of gaps with said second grating orientation $G_{O2}$, the plurality of bars, and the plurality of gaps, with said second grating orientation $G_{O2}$ being arranged periodically; wherein the plurality of gaps of said second grating structure are X-ray transparent; wherein the plurality of bars of said second grating structure are arranged so as to change at least one of phase and amplitude of an X-ray radiation; and wherein said first grating orientation $G_{O1}$ is different than said second grating orientation $G_{O2}$.

16. A diffraction grating configured for X-ray differential phase-contrast imaging, comprising:
a first grating structure that includes a plurality of bars and a plurality of gaps that respectively space apart the plurality of bars, said plurality of bars and the plurality of gaps being disposed in a first grating orientation $G_{O1}$, said plurality of bars, and said plurality of gaps, being arranged periodically; wherein said plurality of bars are arranged such that said plurality of bars change, for X-ray radiation being applied for X-ray differential phase-contrast imaging to said diffraction grating configured for X-ray differential phase-contrast imaging, at least one of phase and amplitude, and wherein said plurality of gaps are X-ray transparent; and, non-overlapping with said first grating structure, a second grating structure that includes a plurality of bars and a plurality of gaps that respectively space apart the plurality of bars of said second grating structure, said plurality of bars of said second grating structure and the plurality of gaps of said second grating structure being disposed in a second grating orientation $G_{O2}$, said plurality of bars, and said plurality of gaps, disposed in said second grating orientation, being arranged periodically; wherein said plurality of bars of said second grating structure are arranged such that said plurality of bars of said second grating structure change, for X-ray radiation being applied for X-ray differential phase-contrast imaging to said diffraction grating configured for X-ray differential phase-contrast imaging, at least one of phase and amplitude, and wherein said plurality of gaps of said second grating structure are X-ray transparent;

wherein said first grating orientation $G_{O1}$ is different than said second grating orientation $G_{O2}$.

17. The diffraction grating of claim 16, wherein said plurality of bars of said first grating structure are straight.

18. The diffraction grating of claim 17, wherein said plurality of bars of said first grating structure are mutually parallel.

19. The diffraction grating of claim 16, wherein said plurality of bars and said plurality of gaps of said first grating structure are disposed individually, by bar and by gap, in said first grating orientation $G_{O1}$, and wherein said plurality of bars and said plurality of gaps of said second grating structure are disposed individually, by bar and by gap, in said second grating orientation $G_{O2}$.

20. A diffraction grating configured for X-ray differential phase-contrast imaging comprising:
multiple first grating structures and multiple second grating structures;
wherein said first grating structure comprises a plurality of bars and a plurality of gaps that respectively space apart said plurality of bars, said plurality of bars and said plurality of gaps being disposed in a first grating orientation $G_{O1}$, said plurality of bars, and said plurality of gaps, being arranged periodically; wherein said plurality of bars are arranged such that said plurality of bars change, for X-ray radiation being applied for X-ray differential phase-contrast imaging to said diffraction grating configured for X-ray differential phase-contrast imaging, at least one of phase and amplitude, and wherein said plurality of gaps are X-ray transparent;

wherein said second grating structure comprises a plurality of bars and a plurality of gaps that respectively space apart the plurality of bars of said second grating structure, said plurality of bars of said second grating structure and said plurality of gaps of said second grating structure being disposed in a second grating orientation $G_{O2}$, said plurality of bars, and said plurality of gaps, disposed in said second grating orientation, being arranged periodically; wherein said plurality of bars of said second grating structure are arranged such that said plurality of bars of said second grating structure change, for X-ray radiation being applied for X-ray differential phase-contrast imaging to said diffraction grating configured for X-ray differential phase-contrast imaging, at least one of phase and amplitude, and wherein said plurality of gaps of said second grating structure are X-ray transparent;

wherein, pairwise from among collectively said multiple first grating structures and said multiple second grating structures, the paired multiple first grating structures and multiple second grating structures are mutually non-overlapping so as to extend a spatial range over which said diffraction grating directly receives incident X-ray radiation; and wherein said first grating orientation $G_{O1}$ is different than said second grating orientation $G_{O2}$.

21. The diffraction grating of claim 20, wherein said plurality of gaps of said first grating structure are individually characterized as having a particular orientation in a plane, said particular orientation being said first grating orientation $G_{O1}$.

22. The diffraction grating of claim 21, wherein said plurality of gaps of said first grating structure individually are elongated.

23. The diffraction grating of claim 20, wherein said multiple first grating structures and said multiple second grating structures are arranged across said spatial range in a chess-board pattern, alternation being based on being either from among said multiple first grating structures or from among said multiple second grating structures.

* * * * *